United States Patent [19]
Lebl

[11] Patent Number: 6,121,054
[45] Date of Patent: Sep. 19, 2000

[54] METHOD FOR SEPARATION OF LIQUID AND SOLID PHASES FOR SOLID PHASE ORGANIC SYNTHESES

[75] Inventor: Michal Lebl, San Diego, Calif.

[73] Assignee: Trega Biosciences, Inc., San Diego, Calif.

[21] Appl. No.: 08/974,090

[22] Filed: Nov. 19, 1997

[51] Int. Cl.[7] .................................................. G01N 1/18
[52] U.S. Cl. .......................... 436/177; 436/45; 436/174; 436/175; 422/68.1; 422/72; 422/101; 422/131; 422/134; 422/136; 530/333; 530/334
[58] Field of Search ................................. 436/43, 45, 47, 436/48, 174, 175, 177; 422/63, 64, 67, 68.1, 72, 101, 131, 134, 136; 530/333, 334, 811, 812, 815, 816; 935/88

[56] References Cited

U.S. PATENT DOCUMENTS

| | | | |
|---|---|---|---|
| 3,586,484 | 6/1971 | Anderson | 436/45 |
| 4,412,973 | 11/1983 | Guigan | 422/72 |
| 5,202,418 | 4/1993 | Lebl et al. | 530/334 |
| 5,338,831 | 8/1994 | Lebl et al. | 530/334 |
| 5,342,585 | 8/1994 | Lebl et al. | 422/131 |
| 5,529,756 | 6/1996 | Brennan | 422/131 |
| 5,605,616 | 2/1997 | Zepp | 205/688 |

FOREIGN PATENT DOCUMENTS

| | | |
|---|---|---|
| 0569115A | 11/1993 | European Pat. Off. . |
| 2156519A | 6/1973 | France . |
| 9310455 | 9/1993 | WIPO . |

OTHER PUBLICATIONS

Birr, 1978, *Aspects of the Merrifield Peptide Synthesis* (Springer–Verlag, New York).

Menotti et al, 1994, *Protein and Peptide Letters* 1 (3):187–192.

*Primary Examiner*—Maureen M. Wallenhorst
*Attorney, Agent, or Firm*—Pennie & Edmonds LLP

[57] ABSTRACT

A simple, efficient apparatus and method for separation of solid and liquid phases useful in methods of high-throughput combinatorial organic synthesis of large libraries or megaarrays of organic compounds is disclosed. The apparatus and method are useful, whether as part of an automated, robotic or manual system for combinatorial organic synthesis. In a preferred embodiment, an apparatus and method of removal of liquid phase from solid phase compatible with microtiter plate type array(s) of reaction vessels is disclosed.

27 Claims, 16 Drawing Sheets

Figure 3D:
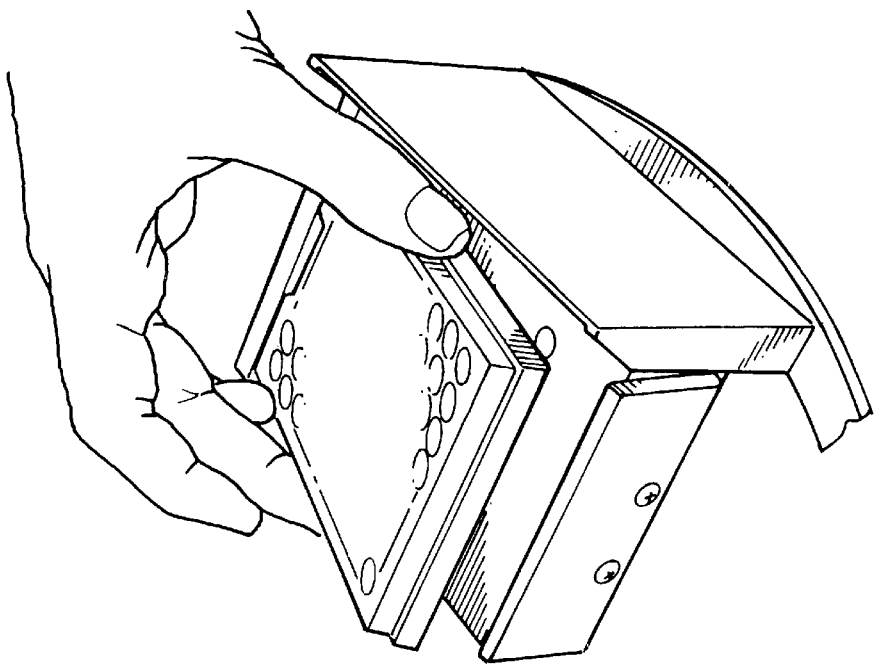
Figure 3C:
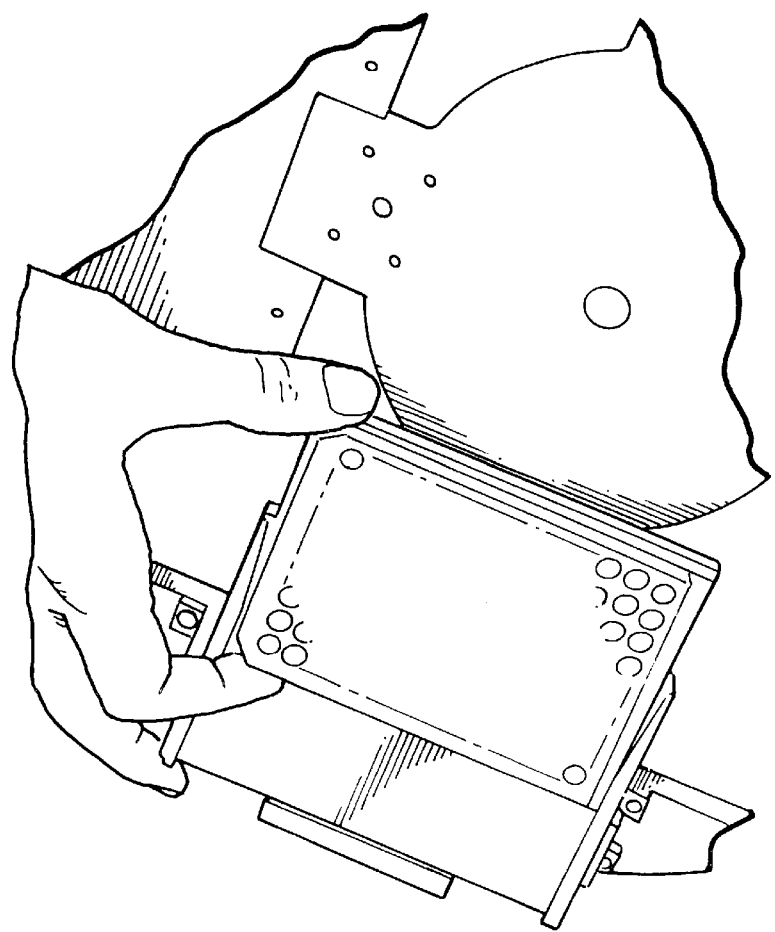
Figure 3F:
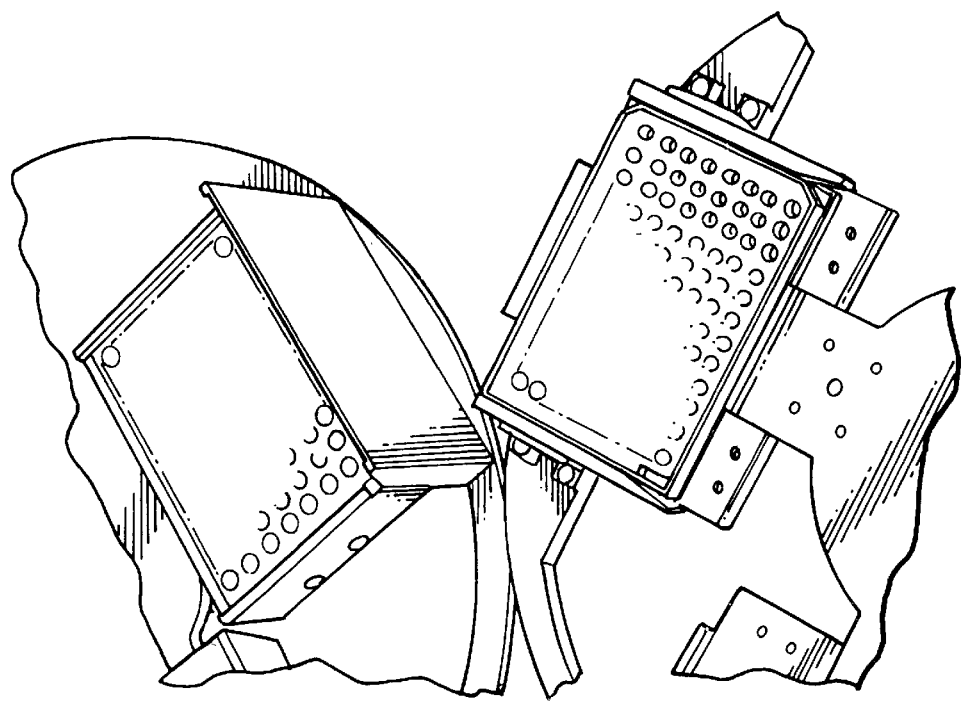
Figure 3E:
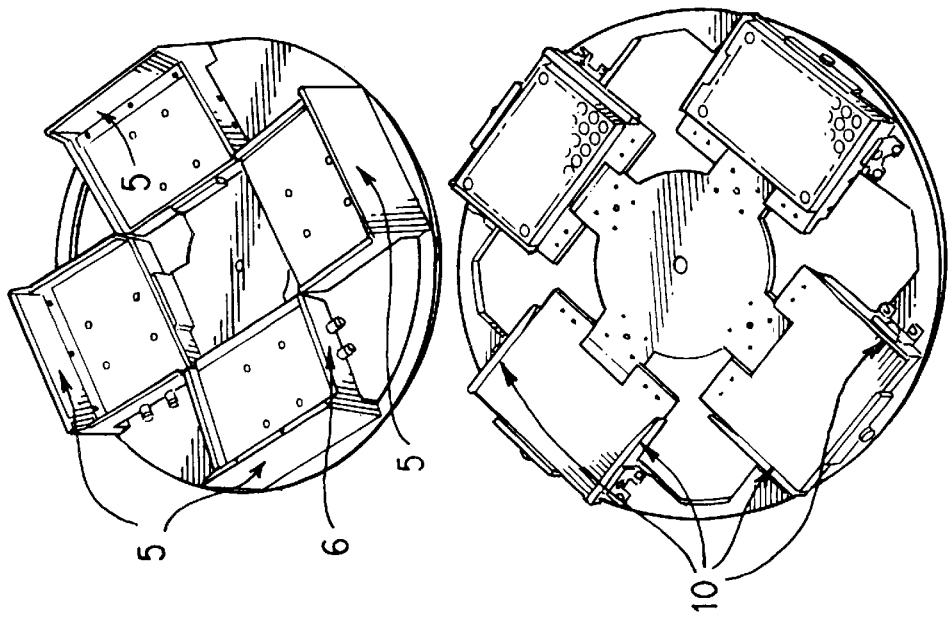

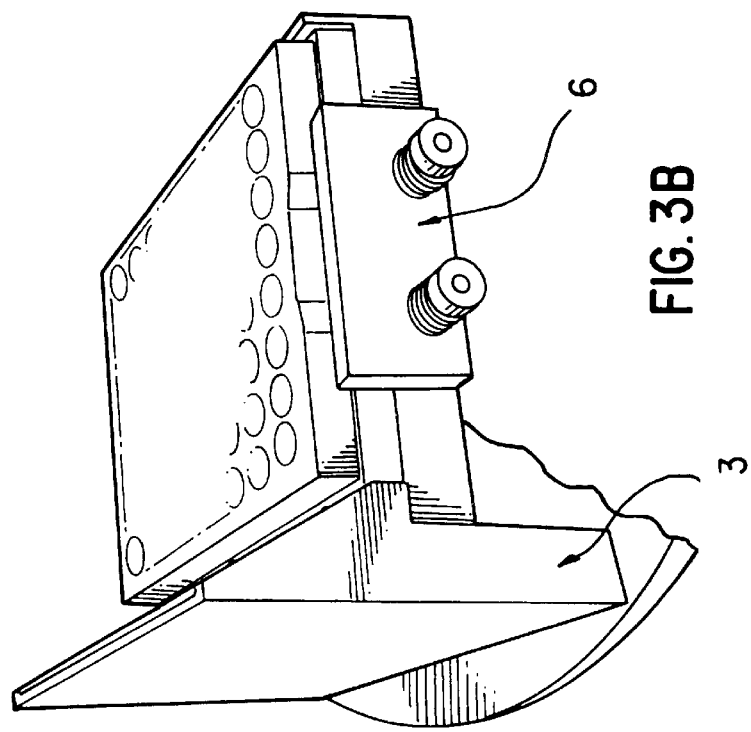
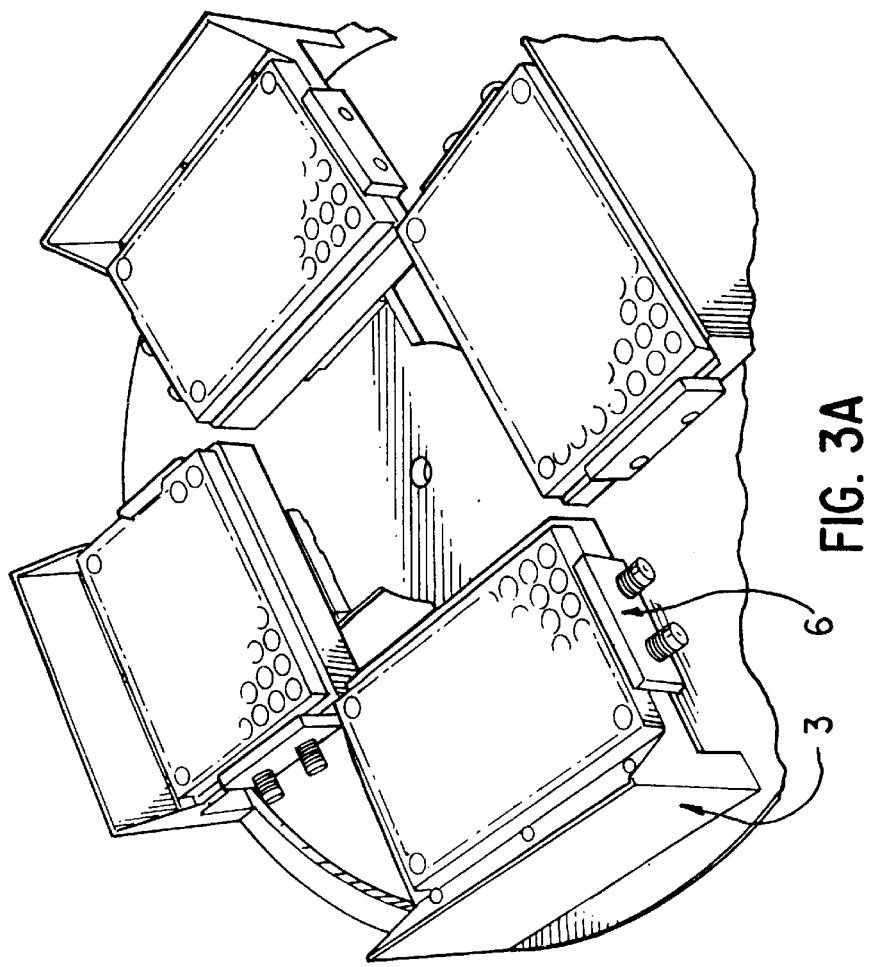
FIG. 3B
FIG. 3A

METHOD FOR SEPARATION OF LIQUID AND SOLID PHASES FOR SOLID PHASE ORGANIC SYNTHESES

1. FIELD OF INVENTION

The present invention relates to the field of devices and methods for chemical synthesis. More particularly, the present invention relates to a simple efficient apparatus and method for separation of solid and liquid phases in high-throughput, solid phase organic synthesis. The present invention is particularly applicable for high-throughput combinatorial synthesis of organic molecules, whether as part of an automated or a manual procedure.

2. BACKGROUND OF THE INVENTION

Solid phase synthesis of organic molecules is the method of choice for preparation of libraries and compound megaarrays, which are currently being applied for screening in the quest to find new drugs or pharmaceutical lead compounds, i.e., compounds which exhibit a particular biological activity of pharmaceutical interest, and which can serve as a starting point for the selection and synthesis of a drug compound, which in addition to the particular biological activity of interest has pharmacologic and toxicologic properties suitable for administration to animals, including humans. Manual synthesis requires repetitions of several relatively simple operations—addition of reagents, incubation and separation of solid and liquid phases, and removal of liquids. This character of the synthetic process renders it optimal for automation. Several designs of automated instruments for combinatorial synthesis have appeared in the patent and non-patent literature. Constructions based on specialized reactors connected permanently (or semi-permanently) to containers for the storage of reagents are strongly limited in their throughput. The productivity of automated instruments can be dramatically improved by use of disposable reaction vessels (such as multititer plates or test tube arrays) into which reagents are added by pipetting, or by direct delivery from storage containers. The optimal storage vehicle is a syringe-like apparatus of a material inert to the chemical reactants, etc., e.g., a glass syringe, allowing the storage of the solution without any exposure to the atmosphere, and capable of serving as a delivery mechanism at the same time. See U.S. Pat. No. 6,045,755 issued on Apr. 4, 2000.

Liquid removal from the reaction vessel (reactor) is usually accomplished by filtration through a filter-type material. The drawback of this method is the potential clogging of the filter, leading to extremely slow liquid removal, or to contamination of adjacent reactor compartments. An alternative technique based on the removal of liquid by suction from the surface above the sedimented solid phase is limited due to incomplete removal of the liquid from the reaction volume. See U.S. Pat. No. 6,045,755 issued on Apr. 4, 2000.

The present application is an improvement upon U.S. Pat. Nos 5,202,418, 5,338,831 and 5,342,585 which describe placement of resin in polypropylene mesh packets and removal of liquid through the openings of these packets (therefore this process is basically filtration), or removal of the liquid from the pieces of porous textile-like material by centrifugation.

Liquid removal by centrifugation was described and is the subject of several publications (see the book "Aspects of the Merrifield Peptide Synthesis" by Christian Birr in the series Reactivity and Structure Concepts in Organic Chemistry vol. 8, K. Hafner, J. -M. Lehn, C. W. Rees, P. von Rague Schleyer, B. M. Trost, R. Zahradnik, Eds., Sringer-Verlag, Berlin, Heidelberg, New York, 1978, and German Patent Application P 20 17351.7, G. 70 13256.8, 1970. These references describe the use of centrifugation for liquid removal from slurry of solid phase particles in a concentrical vessel equipped with a filtration material in its perimeter and spun around its axis.

None of the prior art contemplates the removal of liquid by creation of "pockets" from which material cannot be removed by centrifugal force.

There still remains a need for a simple, efficient means of separating liquid and solid phases during solid phase synthesis of organic molecules, particularly a method amenable to use with automated methods for such syntheses.

3. SUMMARY OF THE INVENTION

The present invention is based on a discovery of a simple efficient means for separation of liquid and solid phases, e.g., removal of liquid from solid phase supports, used for solid phase organic syntheses. In one embodiment of the invention, the solid phase organic synthetic protocol utilizes widely available, disposable reaction vessel arrays, such as microtiter style plates (see FIG. 1A). In an alternative embodiment of the invention, the synthetic protocol utilizes a vessel with a lip facing inward (see FIG. 1B) spun around its axis to create a "pocket" in which the solid material is retained. According to the present invention, however, any vessel or array of vessels or plurality of arrays of vessels which can be placed in a tilted position on the perimeter of a centrifuge, can be used in the method of the invention.

The method of the invention for separating a liquid phase from a solid phase during a solid phase organic synthetic process comprises:

(1) positioning a reaction vessel or an array of reaction vessels, such as a microtiter plate having an array of reaction wells, said vessel(s) containing a sedimentable slurry of solid phase particles or beads in a liquid, on the perimeter of a centrifuge rotor in a tilted or a not tilted position; and (2) spinning the rotor of the centrifuge at a speed so that the solid phase particles sediment in a "pocket" of the vessels and the liquid phase is expelled from the vessels. In one embodiment of the invention, the rotor is spun at a speed so that the centrifugal force on the radius corresponding to the reaction vessels which are closest to the axis of rotation is significantly greater than the force of gravity, and the solid phase particles sediment in a "pocket" of the vessels and the liquid phase is expelled from the vessels. The volume of a "pocket" is determined by: (i) the degree of the tilt, (ii) the speed of rotation, and (iii) the distance of the particular reaction vessel from the axis of rotation. The appropriate combination of these factors determines the volume of residual liquid in the slurry retained in the pocket and therefore completeness of liquid removal. However, since it is desired that all reaction vessels in a multivessel arrangement of a reaction block (such as a microtiter plate) should undergo the removal of the liquid to the same degree, it is important that the angle of the liquid surface in the "pocket" of the reaction vessels during the centrifugation is as close to 90 degrees with respect to the center of rotation as possible. In the situation of a single particle in each of the wells (in the microwell situation (0.05–2 µl volume) or in the case of using macrobeads in a regular well of 20–250 µl volume) even negligible or no tilt successfully retains beads in the wells—there is no force vector pulling the bead out of the pocket, and moreover, partial distortion of the plastic bead due to the centrifugal force prevents the free rolling of otherwise spherical beads.

In one embodiment, the liquid phase is collected on the wall of the centrifuge. In an alternative embodiment, the liquid phase is collected in a "collecting pocket" or a series of "collecting pockets" (see, e.g., FIGS. 3 and 4).

The apparatus of the invention comprises a holder adapted to attaching a reaction vessel or an array of reaction vessels, e.g., a microtiter plate, to a rotor of a centrifuge, said holder comprising one or more indentations or groves designated "collecting pockets" positioned along one side of said holder said collecting pockets having a volume sufficient to collect and retain any liquid expelled from the reaction vessels, e.g., the wells of the microtiter plate, when the holder and attached reaction vessels are spun by the centrifuge rotor. According to the invention, the holder can hold a single or individual microtiter plate or a plurality of microtiter plates, each plate comprising an array of vessels. One or more of the holders can be attached to the rotor of a centrifuge.

In another embodiment, the apparatus of the invention is an automated integrated apparatus or system for solid phase chemical synthesis, comprising:

(a) a centrifuge in which an array of reaction vessels suitable for solid phase organic synthesis can be spun in a tilted or not tilted position;

(b) a liquid distribution device; and (c) a computer for processing a program of instructions for addition of liquid phase to and removal, via centrifugation, of liquid phase from the reaction vessels according to said program.

4. BRIEF DESCRIPTION OF THE FIGURES

Figure 1A:
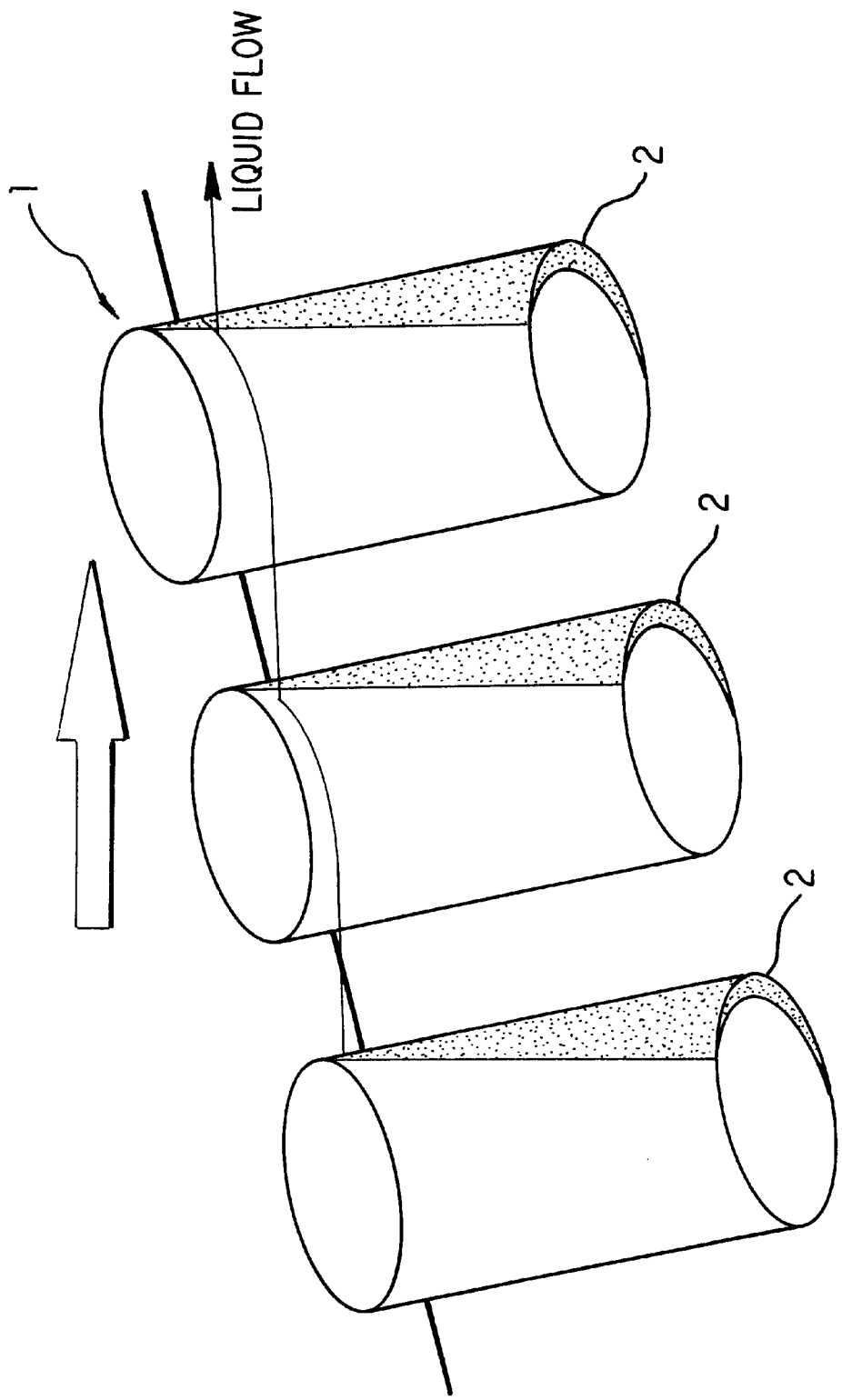
Figure 1B:
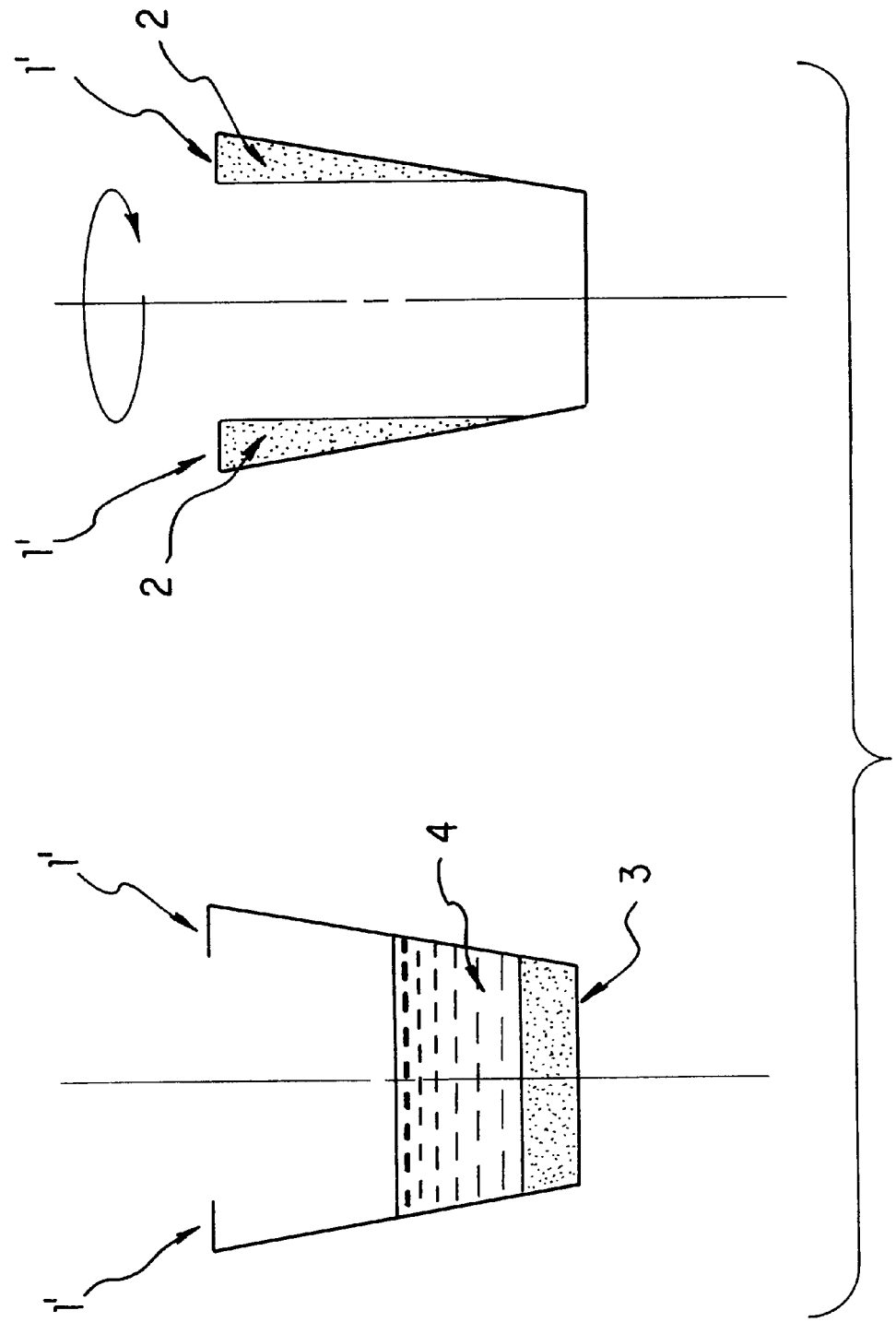

The present invention can be understood more completely by reference to the following detailed description, examples, appended claims and accompanying figures in which:

FIGS. 1(A–B) illustrate sedimentation of solid phase particles in a "pocket" (2) of the vessels and expulsion of liquid achieved according to the method of the invention. FIG. 1A illustrates the path of liquid removed from a vessel, such as a well of a microtiter plate by centrifugation. The straight lip (1) at the upper end of each well of the microtiter plate prevents the liquid from entering the well closer to the edge of a centrifugal plate—this well is higher and the lip wall is tilted in the direction to the bottom of the plate. The large arrow represents the vector resulting from centrifugal and gravitational forces. The small arrow with thin trailing line illustrates the direction of the flow of liquid removed from the reaction vessels. FIG. 1B illustrates an alternative embodiment of the invention in which a vessel having a lip facing inward (1') when spun according to the method of the invention "creates" a "pocket" (2) in which the solid phase particles are retained. The left portion of FIG. 1B illustrates the solid phase (3) and liquid phase (4) in the vessel prior to centrifugation. The right portion of FIG. 1B illustrates the pocket (2) containing retained solid phase during spinning (and removal of the liquid).

Figure 2A:
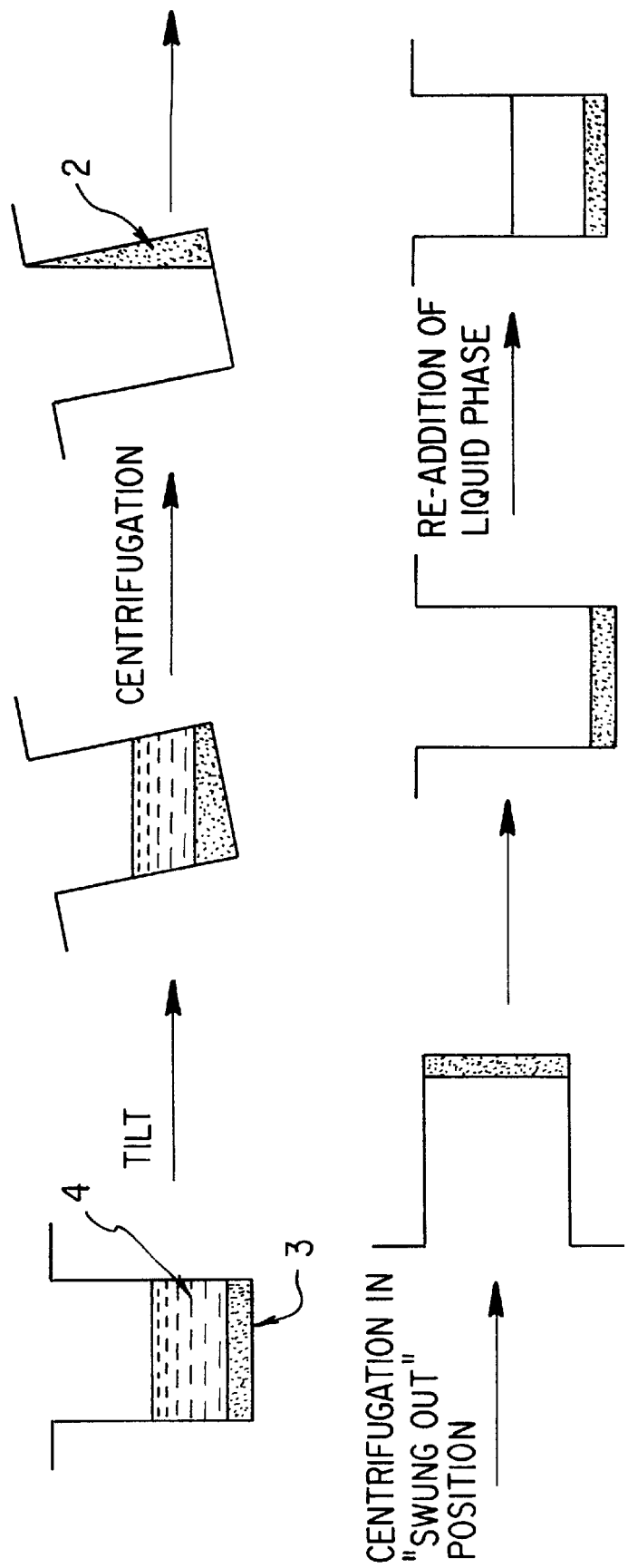
Figure 2B:
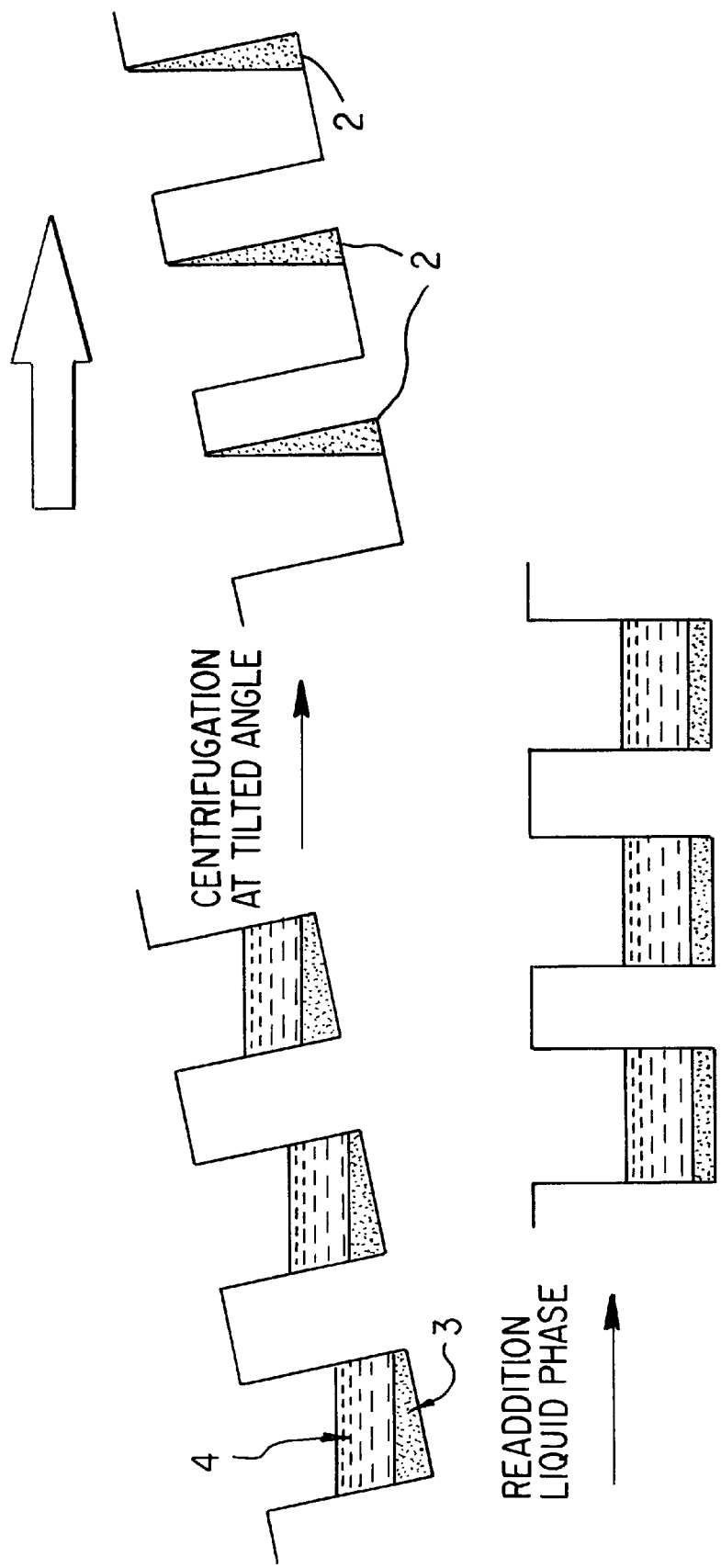

FIGS. 2(A–B) illustrate a number of embodiments of the separation apparatus/process of the present invention using a single or individual well-type reaction vessel (FIG. 2A); and an embodiment using a multi-well microtiter-type plate or array of reaction vessels (FIG. 2B). As shown in FIG. 2A, continued centrifugation, in a "swung out" position, after centrifugal expulsion of the liquid, allows the solid phase particles to fill from the pocket (2) to the bottom of the vessels.

FIGS. 3(A–F) illustrate a variety of embodiments of means for attaching one or a plurality of microtiter plates to a centrifuge rotor according to the method of the invention. FIG. 3A shows four microtiter plates, in a single layer, attached to a rotor of a centrifuge. A spring loaded side wall (6) aids in keeping the microtiter plate securely affixed. FIG. 3B is an enlarged illustration of one of the microtiter plates shown in FIG. 3A. A hollow "collecting pocket" (5) at the edge of the microtiter holders is illustrated. The collecting pocket receives and retains the liquid phase expelled from the microtiter wells during centrifugation. FIGS. 3C and 3D demonstrate different ways to attach the plates to the rotor. FIG. 3C shows sliding the plate into two rails from the inside (3C) and FIG. 3D shows snapping it in against a spring loaded side wall (6). FIGS. 3E and 3F illustrate two means for attaching the microtiter plates. The top portion of FIG. 3E shows a means in which a spring loaded side wall (6) can "clamp" a microtiter plate to the holder. The lower portion of FIG. 3E shows a means in which two parallel "guard rails" (10) along the side walls retain the microtiter plate in place on the holder. FIG. 3F (top and lower positions) is an enlarged view of the holders shown in FIG. 3E.

Figure 4:
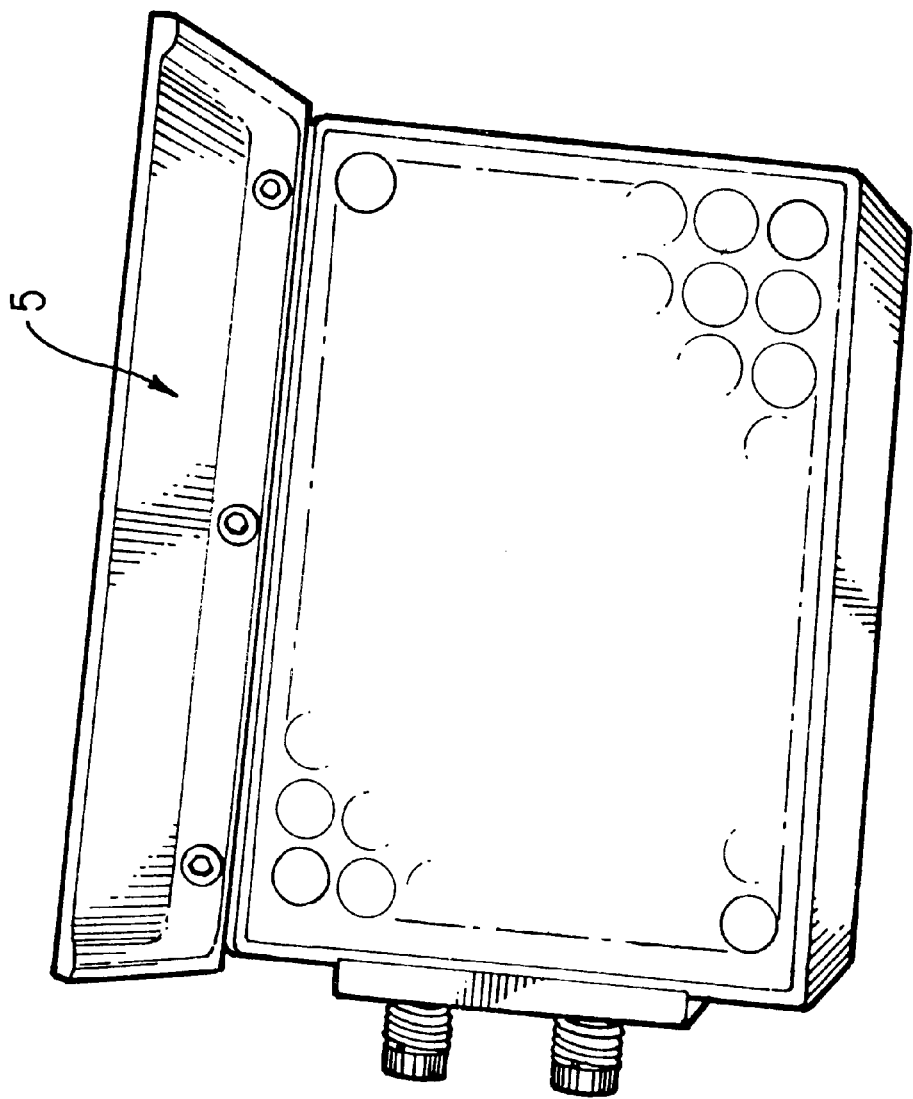

FIG. 4 is an enlarged top view of the microtiter plate affixed to a rotor shown in FIG. 3A. The collecting pocket(s) which collects the liquid phase expelled from the microtiter wells during centrifugation is clearly visible.

FIGS. 5(A–D) illustrate a plurality of microtiter plates positioned in a housing (7) which can hold several plates and which is used to attach the plurality of microtiter plates to a centrifuge rotor according to the method of the invention. FIG. 5A depicts four closed housings (7) positioned on a rotor, each of which housings can hold four microtiter plates or a total of 16 microtiter plates for the four housings illustrated. FIG. 5B illustrates a detachable retainer wall (8) with a hollow "shoe" (9) which can be used to close the housing (7). During centrifugation, the liquid expelled from the wells of the microtiter plates collects in the hollow shoe (9). FIG. 5C shows four microtiter plates positioned in a housing (7). FIG. 5D illustrates the plate tilt of the microtiter plates in the housing.

Figure 6A:
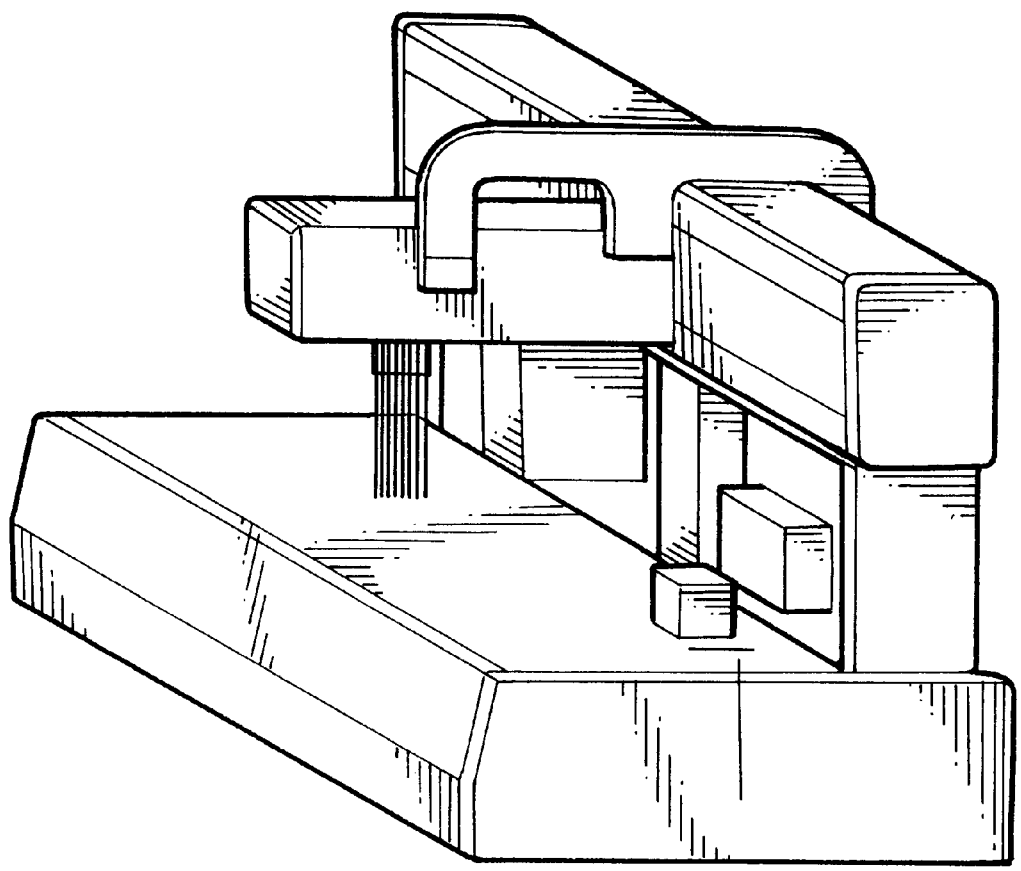
Figure 6B:
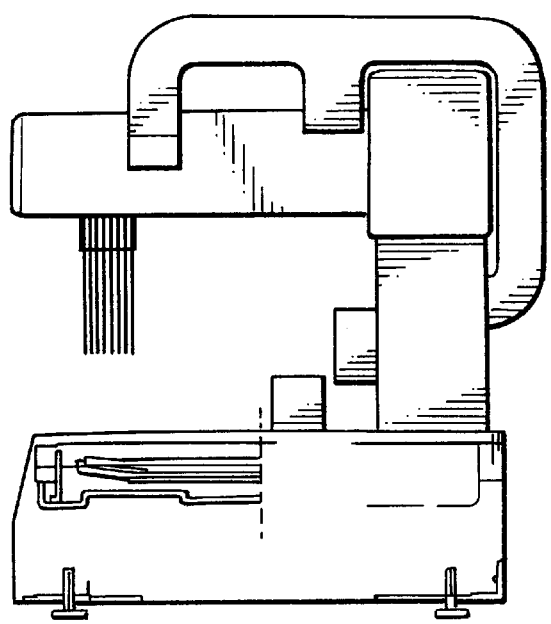
Figure 6C:
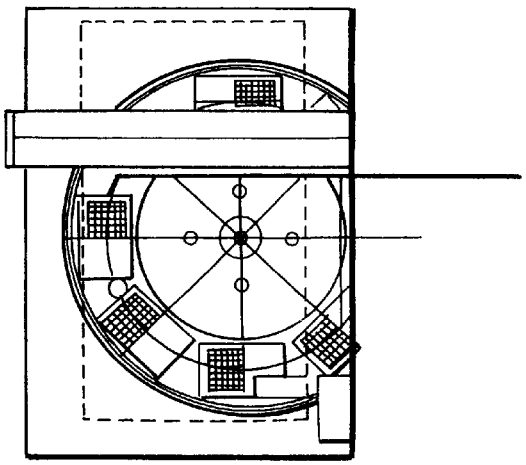

FIGS. 6(A–C) illustrate a centrifuge integrated with a liquid distribution system useful according to the method of the present invention. The integrated centrifuge and liquid distribution system can be combined with a computer for processing of instructions for addition to and removal of liquid phase from the reaction vessels to provide an integrated apparatus or system useful for solid phase synthesis of compounds or libraries of compounds. FIG. 6A is a general view showing a centrifuge positioned under a liquid distribution system; FIG. 6B is a side view; and FIG. 6C is a top view showing microtiter plates positioned for centrifugation.

Figure 7B:
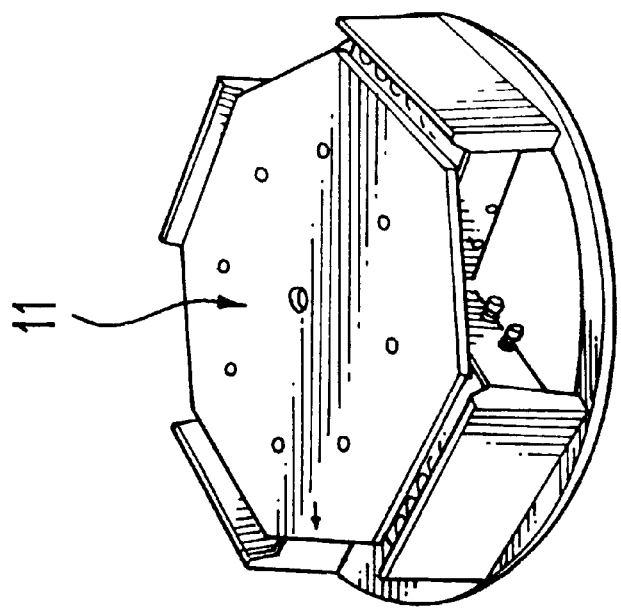
Figure 7A:
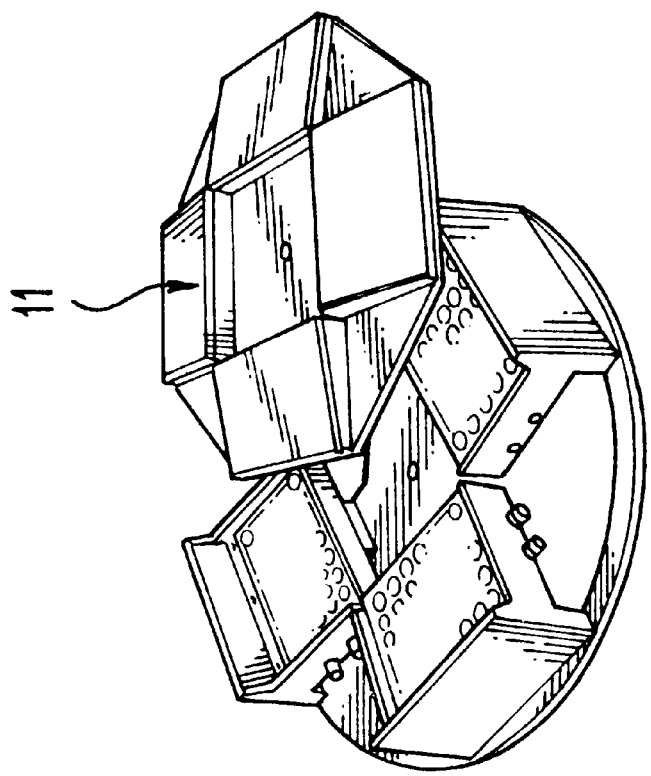

FIGS. 7(A–B) illustrate complementary "rotor cover" (11) and plates sandwiched between the rotor and rotor cover for high temperature incubation.

FIGS. 8(A–C) demonstrate that there is no transfer of solid phase from one well to another. The arrows indicate the direction of centrifugal force applied to the plate. FIGS. 8A–B are views through a binocular dissecting microscope of two microtiter plate wells, one originally containing solid and liquid phases placed closer to the center of rotation and one empty well placed further away from the center of rotation, after passing through several steps of centrifugal liquid removal. FIG. 8A shows the situation in which the well was not "overloaded" with solid phase. FIG. 8B shows the situation in which the well was "overloaded" with the solid phase (resin)—capacity of the pocket was not adequate (12 mg). However, even in this situation the resin was not transferred to the next well. FIG. 8C also shows a microtiter plate "overloaded" with solid phase (upper plate on left part of FIG. 8C). The redundant resin ended in the "interwell" space, as illustrated by left upper plate in FIG. 8C. The right panel of FIG. 8C is an enlarged version of the upper plate of the left panel to show closer details.

Figure 9B:
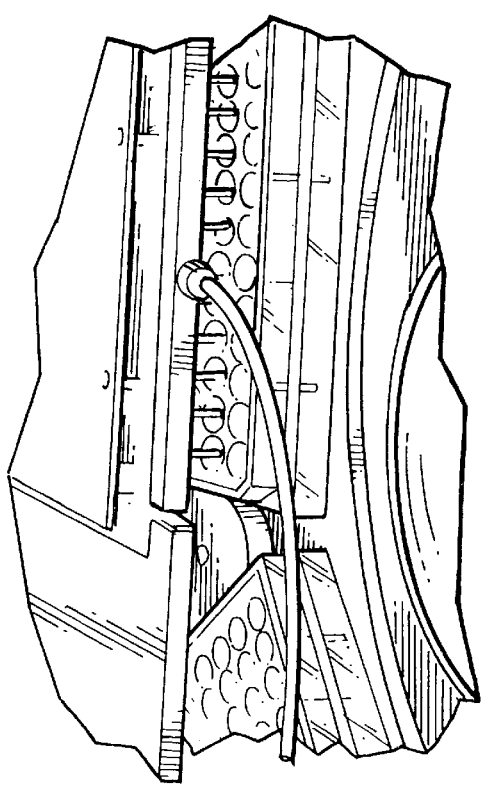
Figure 9C:
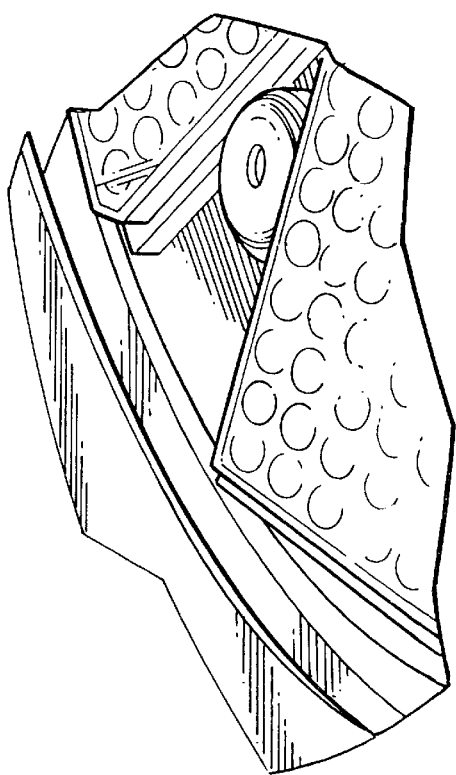
Figure 9A:
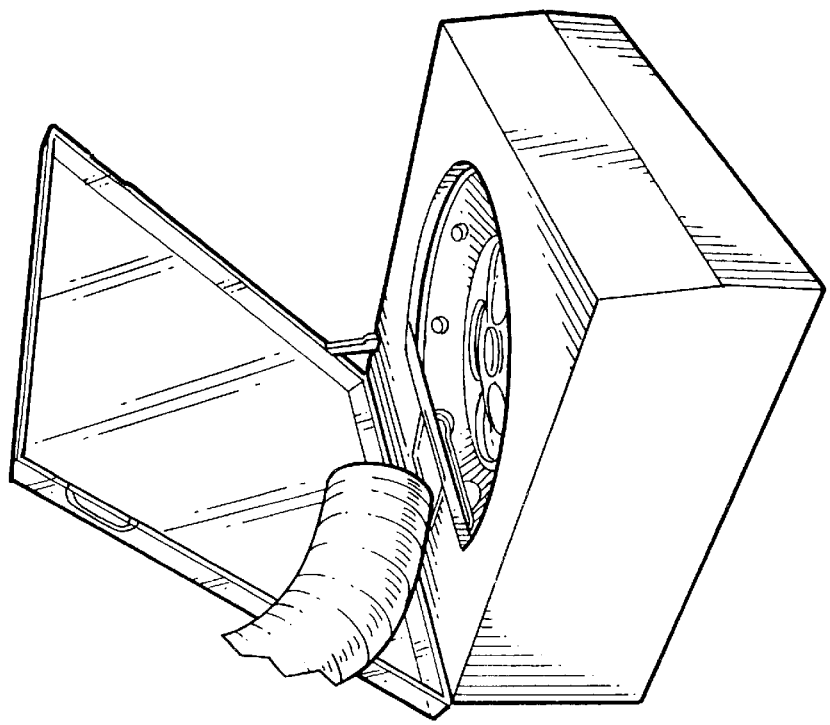

FIGS. 9(A–C) illustrate a centrifuge built according to the present invention as a centrifuge-based solid phase synthetic apparatus. The system has an integrated 96 channel liquid distribution system. FIG. 9A shows a centrifuge useful as a solid phase synthesizer in which tilted plates are centrifuged. This centrifuge has a rotor of a diameter 25 cm, on the perimeter of which are placed eight microtiter plates in permanent tilt of 9 degrees. The centrifuge is integrated with a 96 channel liquid distributor which can deliver solvent or solutions of reagents from six different bottles into the plate positioned under the needles of the distributor. FIG. 9B shows the rotor of the centrifuge and FIG. 9C shows the detail of the microtiterplate attachment to the rotor.

5. DETAILED DESCRIPTION OF THE INVENTION

For clarity of disclosure, and not by way of limitation, the detailed description of this invention is presented herein with respect to figures that illustrate preferred embodiments of elements of this invention. However, this invention includes those alternative embodiments of these elements performing similar functions in similar manners that will be apparent to one skilled in the art from the entirety of the disclosure provided.

By way of introduction, combinatorial chemistry synthesis protocols prescribe the stepwise, sequential addition of building blocks to intermediate and/or partially- synthesized intermediate compounds in order to synthesize a final compound.

In solid-phase synthesis, final compounds are synthesized attached to solid-phase supports that permit the use of simple mechanical means to separate intermediate, partially-synthesized intermediate compounds between synthetic steps. Typical solid-phase supports include beads, including microbeads, of 30 microns to 300 microns in diameter, which are functionalized in order to covalently attach intermediate compounds (or final compounds), and made of, e.g., various glasses, plastics, or resins.

Solid-phase combinatorial synthesis typically proceeds according to the following steps. In a first step, reaction vessels are charged with a solid-phase support, typically a slurry of functionalized beads suspended in a solvent. These beads are then preconditioned by incubating them in an appropriate solvent, and the first of a plurality of building blocks, or a linker moiety, is covalently linked to the functionalized beads. Subsequently, a plurality of building block addition steps are performed, all of which involve repetitive execution of the following substeps, and in a sequence chosen to synthesize the desired compound. First, a sufficient quantity of a solution containing the building block moiety selected for addition is accurately added to the reaction vessels so that the building block moiety is present in a molar excess to the intermediate compound. The reaction is triggered and promoted by activating reagents and other reagents and solvents, which are also added to the reaction vessel. The reaction vessel is then incubated at a controlled temperature for a time, typically between 5 minutes and 24 hours, sufficient for the building block addition reaction or transformation to go to substantial completion. Optionally, during this incubation, the reaction vessel can be intermittently agitated or stirred. Finally, in a last substep of building block addition, the reaction vessel containing the solid-phase support with attached intermediate compound is prepared for addition of the next building block by removing the reaction fluid and thorough washing and reconditioning the solid-phase support. Washing typically involves three to seven cycles of adding and removing a wash solvent. Optionally, during the addition steps, multiple building blocks can be added to one reaction vessel in order to synthesize a mixture of compound intermediates attached to one solid-phase support, or alternatively, the contents of separate reaction vessels can be combined and partitioned in order that multiple compounds can be synthesized in one reaction vessel with each microbead having only one attached final compound. After the desired number of building block addition steps, the final compound is present in the reaction vessel attached to the solid-phase support. The final compounds can be utilized either directly attached to the synthetic supports, or alternatively, can be cleaved from the supports and extracted into a liquid phase.

An exemplary solid-phase combinatorial protocol is that for the synthesis of peptides attached to polymer resin, which proceeds according to Lam et al., 1991, A new type of synthetic peptide library for identifying ligand-binding activity, *Nature* 354:82–84. U.S. Pat. No. 5,510,240 to Lam et al. for Method of screening a peptide library; Lam et al., 1994, Selectide technology: Bead-binding screening. *Methods: Companion to Methods in Enzymology* 6:372–380. Another exemplary protocol is that for the synthesis of benzodiazepine moieties, which proceeds according to Bunin et al., 1992, A general and expedient method for the solid phase synthesis of 1,4-benzodiazepine derivatives, *J. Amer. Chem. Soc.*, 114:10997–10998. U.S. Pat. No. 5,288,514 to Ellman for Solid phase and combinatorial synthesis of benzodiazepine compounds on a solid support. Also, for protocols for the addition of N-substituted glycines to form peptoids, see, e.g., Simon, et al., 1992, Peptoids: A modular approach to drug discovery. *Proc. Natl. Acad. Sci. USA*, 89:9367–9371; Zuckermann et al., 1992, Efficient method for the preparation of peptoids [oligo(N-substituted glycines)] by submonomer solid-phase synthesis. *J. Amer. Chem. Soc.*, 114:10646–10647; WO PCT94/06,451 to Moos et al. for Synthesis of N-substituted polyamide monomers, useful as solvents, additives for food, enzyme inhibitors etc. Approaches for synthesis of small molecular libraries were recently reviewed by, e.g., Krchnak and Lebl, 1996, Synthetic library techniques: Subjective (biased and generic) thoughts and views, *Molecular Diversity*, 1:193–216; Ellman, 1996, Design, synthesis, and evaluation of small-molecule libraries, *Account. Chem. Res.*, 29:132–143; Armstrong et al., 1996, Multiple-component condensation strategies for combinatorial library synthesis, *Account. Chem. Res.*, 29:123–131.; Fruchtel et al., 1996, Organic chemistry on solid supports, *Angew. Chem. Int. Ed.*, 35:17–42; Thompson et al., 1996, Synthesis and application of small molecule libraries, *Chem. Rev.*, 96:555–600; Rinnova et al., 1996, Molecular diversity and libraries of structures: Synthesis and screening, *Collect. Czech. Chem. Commun.*, 61: 171–231; Hermkens et al., 1996, Solid-phase organic reactions: A review of the recent literature, *Tetrahedron*, 52:4527–4554. Exemplary building blocks and reagents are amino acids, other organic acids, aldehydes, alcohols, and so forth, as well as bifunctional compounds, such as those given in Krchnak and Lebl, 1996, Synthetic library techniques: Subjective (biased and generic) thoughts and views, *Molecular Diversity*, 1:193–216.

5.1. PROCESS

The method of the invention for separating a liquid phase from a solid phase during a solid phase organic synthetic process comprises:

(1) positioning a reaction vessel or one or more arrays of reaction vessels, such as one or more microtiter plates, said vessels containing a slurry of solid phase particles or beads in a liquid, on the perimeter of a centrifuge rotor in a tilted or not tilted position; and (2) spinning the rotor of the centrifuge at a speed so that the solid phase particles sediment in a "pocket" of the vessels and the liquid phase is expelled from the vessels.

In the case of situation in which only one row of vessels is placed at the perimeter of the centrifuge rotor, the ratio of centrifugal force versus gravitation determines the volume of the "pocket" used for the separation of solid and liquid phase in all vessels and even very low ratio (such as 1:1) can be successfully used. The important factor is only the reproducibility of the speed of centrifugation.

In one embodiment of the invention, the rotor of the centrifuge is spun at a speed so that the centrifugal force on the radius corresponding to the reaction vessels which are closest to the axis of rotation is significantly greater than the force of gravity so that the solid phase particles sediment in a "pocket" of the vessels and the liquid phase is expelled from the vessels. The volume of a "pocket" is determined by: (i) the degree of the tilt, (ii) the speed of rotation, and (iii) the distance of the particular reaction vessel from the axis of rotation. The appropriate combination of these factors determines the volume of residual liquid in the slurry retained in the pocket and therefore completeness of liquid removal. However, since it is desired that all reaction vessels in a multivessel arrangement or array of vessels (such as a microtiter plate) should undergo the removal of the liquid to the same degree, it is important that the angle of the liquid surface in the "pocket" of the reaction vessels during the centrifugation is as close to 90 degrees with respect to the axis of rotation as possible. In the case when a single particle is used in each of the wells (e.g., using a microwell situation (0.05–2 μl volume) or in the case when using macrobeads in a regular well (20–250 μl volume) even negligible or no tilt successfully retains beads in the wells—there is no force vector pulling the bead out of the pocket, and moreover, partial distortion of the plastic bead due to the centrifugal force prevents the free rolling of otherwise spherical beads.

As used in the present application, the term "significantly greater than the force of gravity" is intended to mean that the force is at least about 5 to 300× G, preferably about 10 to 300× G, and even more preferably about 100 to 300× G. In other words, the centrifuge is spun at a speed so that the ratio of the centrifugal force to gravity, i.e., the Relative Centrifugal Force (RCF) is at least about 5 to 300, preferably about 10 to 300, and more preferably about 100 to 300.

RCF can be calculated according to the following formula:

$$RCF = 0.000018 \times r \times N^2$$

where r is the radius of rotation in centimeters and N is the rotating speed in revolutions per minute (rpms).

For example, if r is 17 cm and the rotor is spun at 350 rpms, the Relative Centrifugal Force is 23 times greater than gravity (G). If r is 23 cm and the rotor is spun at the same speed, the RCF is 31.5× G.

Values of RCF significantly greater than 1 are required if individual vessels are placed at different distances from the center of rotation. To achieve uniform distribution of liquid in all vessels it is important to remove as much as possible of the liquid phase from all wells. The theoretical value of an angle of liquid surface achievable in the centrifuge versus liquid in nondisturbed state is 90 degrees. This requires a value of the above mentioned ratio (RCF) reaching infinity. For practical reasons, the difference between 89 degrees (ratio 100:1) or 85 degrees (ratio 18:1) may be acceptable. Acceptability of this value depends on the degree of the tilt determining the absolute value of the "pocket" volume. The greater the tilt, the bigger the "pocket" volume, and the bigger the tolerance to the different ratio values at different radiuses. The maximal possible value of the tilt in "fixed tilt" centrifuges is 45 degrees, however, this tilt is completely impractical because the maximal volume of liquid in the well is equal to the volume of the theoretical "pocket". Higher tilt is possible in the case of "dynamically adjustable tilt" centrifuges (centrifuges in which plate is horizontal in standstill state and "swings out" to a limited position during rotation). In the above given example the angle of the pocket liquid level is 86.1 degrees for the "inner" wells, versus 87.25 degrees for the "outer" walls.

According to one mode of one embodiment of the method of the invention, when the reaction vessels used are one or more arrays of regular wells in a microtiter plate, the rotor of the centrifuge is spun at a speed so that the centrifugal force on the radius of wells closest to the axis of rotation is a about 5 to 300× G, preferably about 10 to 300× G, and more preferably about 100 to 300× G; and the angle of tilt of the plate is about 1 to 45, preferably 5 to 20, and more preferably 5 to 15 degrees. According to another mode of this embodiment of the method of the invention, when the reaction vessels used are one or more arrays of microwells in a microtiter plate, the rotor of the centrifuge is spun at a speed so that the centrifugal force on the radius of wells closest to the axis of rotation is about 5 to 300×G, preferably about 10 to 300× G, and more preferably about 100 to 300× G and the angle of tilt of the plate is about 0 to 25, preferably 0 to 10, and more preferably 0 to 2 degrees.

In one embodiment, the liquid phase is collected on the wall of the centrifuge. In an alternative embodiment, the liquid phase is collected in a "collecting pocket" (5) or a series of "collecting pockets". See generally FIGS. 3 and 4 for illustration of the collecting pocket (5).

FIGS. 1(A–B) illustrate sedimentation of solid phase particles in a "pocket" (2) of the vessels and expulsion of liquid achieved according to the method of the invention. FIG. 1A illustrates the path of liquid removed from a vessel, such as a well of a microtiter plate by centrifugation. The straight lip (1) at the upper end of each well of the microtiter plate prevents the liquid from entering the well closer to the edge of a centrifugal plate—this well is higher and the lip wall is tilted in the direction to the bottom of the plate. The large arrow represents the vector resulting from centrifugal and gravitational forces. The small arrow with thin trailing line illustrates the direction of the flow of liquid removed from the reaction vessels. FIG. 1B illustrates an alternative embodiment of the invention in which a vessel having a lip facing inward (1') when spun according to the method of the invention "creates" a "pocket" (2) in which the solid phase particles are retained. The left portion of FIG. 1B illustrates the solid phase (3) and liquid phase (4) in the vessel prior to centrifugation. The right portion of FIG. 1B illustrates the pocket (2) containing retained solid phase during spinning (and removal of the liquid).

FIG. 2A generally illustrates the process of the invention in which a single reaction vessel is used.

FIG. 2B generally illustrates the process of the invention in which a microtiter plate serves as the array of reaction vessels.

As detailed above, a single reaction vessel, a single microtiter plate or a plurality of microtiter plates can be used in the process of the present invention. Merely, for ease of explanation, and not be way of limitation, the description below relates to use of a microtiter plate as an array of reaction vessels. This is in no way intended to limit the process of the invention.

Slurry of a solid phase support is distributed into the wells of a standard, e.g., polypropylene, microtiter plate either manually, e.g., by multichannel pipetting of nonsedimenting (isopycnic) suspension, or automatically, e.g., by application of the instrument described in patent application Ser. No. 08/815,975 (see Section 5.3.3. "Fluid Slurry Dispensing Means" at pages 58–63, incorporated herein by reference). In the case of isopycnic suspensions, low density solvent is added to effect sedimentation of the solid support, e.g., beads. The microtiter plate is then placed on the perimeter of a centrifuge rotor in a tilted position. The tilt for a standard microtiter plate in which each well contains about 5 mg of swollen polymer resin (beads of solid phase) is about not greater than 9 degrees tilting towards the center of the rotation.

The microtiter plate is attached to the rotor by any means suitable for maintaining the microtiter plate at the proper tilt angle during centrifugation. See Section 5.2., infra, for illustrative embodiments, of holders housings, etc. which can be used for attachment of a microtiter plate or an array or plurality of microtiter plates to a centrifuge rotor.

The best way to find optimal solid support load for particular microtiterplate type, type of solid support, and tilt angle is the experiment in which wells of the plate are loaded with higher amount of the resin (approximately 10 mg) and resin is suspended in liquid phase and centrifuged several times. Residual resin weight in individual wells is then determined either directly (weighing) or indirectly (quantitative determination of compound bound to the resin of known capacity).

The microtiter plate or array of microtiter plates is then spun at a speed so that the solid phase supports sediment in a "pocket" of the tilted microtiter plate. According to one embodiment, the centrifuge is spun at a speed at which the centrifugal force on the radius corresponding to the wells which are closest to the axis of rotation is significantly greater than the force of gravity, as described above. At this speed, the solid phase supports in the wells sediment in a "pocket" formed by the tilted microtiter plate.

To achieve uniformity of the pocket size, the microtiter plate is preferably placed on the perimeter of a rotor which has a radius which is at least three times the width of a microtiter plate since then the difference in centrifugal force on the wells on the shorter radius versus that force on the wells on the long radius (i.e., the difference in force on the inner and outer wells) will be advantageously small. Liquid volume larger than the "pocket" volume is expelled from the well and travels following the trajectory dictated by the sum of the centrifugal and gravitational force and is collected on the walls of the centrifuge. Alternatively, the expelled liquid is collected in one or more collecting pockets (see, e.g., FIGS. 3–4).

One or more wash solution(s) for the combinatorial organic synthetic process are delivered by a multichannel distribution device positioned above the microtiter plate or arrays of microtiter plates. The most preferable arrangement of the centrifuge is a rotor directly coupled to a stepper motor which can be precisely controlled by a computer, and which can position the microtiter plate or arrays of microtiter plates under particular delivery head as needed.

One embodiment of the process/apparatus of the invention for use with an automated system is depicted in FIGS. 9(A–C). A round centrifugal plate tilted towards the center is equipped with eight knobs (FIG. 9C) under which the microtiter plate can be slided. Outer edge of the centrifugal plate serves as the positional limitation of the microtiter plate. An alternative placement of the microtiter plates is placement on a swinging holder which can be tilted and/or released for the full swing—in the latter case the liquid is held inside of the wells of microtiter plate and does not "bump" even when the vacuum is applied. This position can be used for drying the content of the plate or for pulling down the solid material from the sides of the well after centrifugation in tilted position. Such alternative placement is referred to herein as centrifugation in a "swung-out" mode.

As will be understood by those skilled in the art, any vessel, array of vessels, or plurality of arrays of vessels, which can be placed in a tilted position on the perimeter of a centrifuge can be used according to the process of the invention to create a "pocket" during centrifugation in which a solid phase can be retained and from which liquid can be expelled.

As indicated above, reaction vessel arrays useful in one embodiment of the process of this invention comprise various commercially available microtiter-like plates (or a plurality thereof) having arrays of wells. Exemplary of such commercially available plates are standard microtiter plates with an 85×130 mm footprint and having a rectangular array of 96, 384 or more wells. Normal or deep well microtiter plates made of solvent resistant material can be used in this embodiment.

After attachment to the rotor of the centrifuge, the microtiter plate is tilted by adjustment of the swivel of the holding plate.

The angle of the tilt depends on the amount of the solid support in each of the wells. The optimal tilt is such that only swollen solid remains in the well and basically all liquid is expelled. In one mode of the process, after stopping the rotation, the swinging holding plate swings back to parallel position and microtiter plate is placed (rotor is turned) under the multichannel liquid delivery head. The wash solvent is delivered, the tilt limiting mechanism is released, and the plate is rotated at a high speed to assure that the solid phase is transferred from the "pocket" onto the bottom of each well of the microtiter plate.

In an alternative mode, the tilt limiting mechanism is not released and the rotor is spun at the speed at which the liquid phase is just reaching the edge of the well, thus wetting all solid support in the "pocket". This speed can be determined experimentally by slowly increasing the centrifuge speed and following the level of liquid by observation under stroboscopic light synchronized to the rotation speed.

Microtiter plates are optionally stirred by oscillating between the slow rotation and rotation at the speed close but lower than the "highest allowable speed still not spilling the liquid" (HASSNSL), or by stepping the stepper motor back and forth in a fast succession. After shaking, the tilt limitation is kept and plates are spun at the high speed.

The whole process is repeated as many times as many washes are required. In the case of multilayered arrangement, (see, e.g., FIGS. 5A and B) or array of microtiter plates, the multichannel distributor is inserted individually along each layer of microtiter plate and liquid is delivered in several stages. Alternatively, the multilayered delivery system can be used. After the last wash, the microtiter plate can be centrifuged in vacuum to remove the last portions of the washing solvent. After stopping and proper positioning the building blocks can be delivered into, this now parallely positioned, or still tilted, microtiter plate by pipetting from stock solutions, by direct delivery from syringes used for storage of building blocks, or by ink-jet systems. Plates can than be stoppered either by compliant sheet like material (teflon coated silicon rubber sheets) pressed against the plates in a form a complementary "cover rotor" (see FIGS. 7A and B), or by application of individual plate covers in shape of inert (teflon) balls in flexible arrays (see, e.g., U.S. Pat. No. 6,045,755 issued on Apr. 4, 2000 Section 5.2.2 "Microtiter-Style Reaction Vessels" at pages 30–34 incorporated herein by reference. The closed microtiter plates can then be placed on a shaker or in an oven for high temperature incubation. The whole operation of washing and building block addition can be performed in a centrifuge completely closed and filled with an inert atmosphere, thus allowing to perform highly air or moisture sensitive reactions.

5.2. APPARATUS

The apparatus of the invention comprises a holder(s) adapted to attaching a microtiter plate or a plurality of microtiter plates to a rotor of a centrifuge in a tilted arrangement. The holder(s) may either hold one or more of the microtiter plates in a fixed tilted position or in a position in which the angle of tilt can be changed flexibly. The holders adapted to attaching a microtiter plate to a centrifuge rotor can have or comprise a series of collecting pockets (5) to collect and retain the liquid expelled from the vessels during centrifugation. See, for example, FIGS. 3A, B, E, F and FIG. 4 which illustrate the collecting pockets (5). The holder(s) illustrated by FIG. 3E, for example, comprise(s) one or more indentations or groves designated "collecting pockets" having a volume sufficient to collect and retain any liquid expelled from the wells of the microtiter plate(s) when the holder and attached microtiter plate are spun by the centrifuge rotor.

In an alternative embodiment, the holder does not have collecting pockets. In the latter situation, the liquid expelled is deposited on the walls of the centrifuge.

As indicated above, (see FIGS. 3A–3F), a single layer of microtiter plates can be attached by means of holders to the centrifuge rotor. Placing of individual microtiter plates on the centrifuge perimeter has an advantage of simple interfacing with liquid distribution automats (such as Packard Canberra, Tecan, Hamilton, and others).

FIGS. 6(A–C) illustrate an integrated device in which a liquid distribution device is placed onto the top of a centrifugal synthesizer. The integrated device is useful as a "centrifugation synthesizer" for solid phase synthetic processes.

According to an alternative embodiment, a multi-layered array of microtiter plates can be attached by means of holders to the centrifuge rotor. Any convenient means for holding the multi-layered array(s) of microtiter plates to the rotor can be used.

FIGS. 5(A–D) illustrate placement of a plurality of microtiter plates in housings, in which each microtiter plate can be slipped in along "rails" to position it inside the housing attached to a centrifuge rotor in a tilted position. As shown, four microtiter plates can be positioned in four housings, thus holding 16 microtiter plates in a tilted position on the rotor.

Figure 5B:
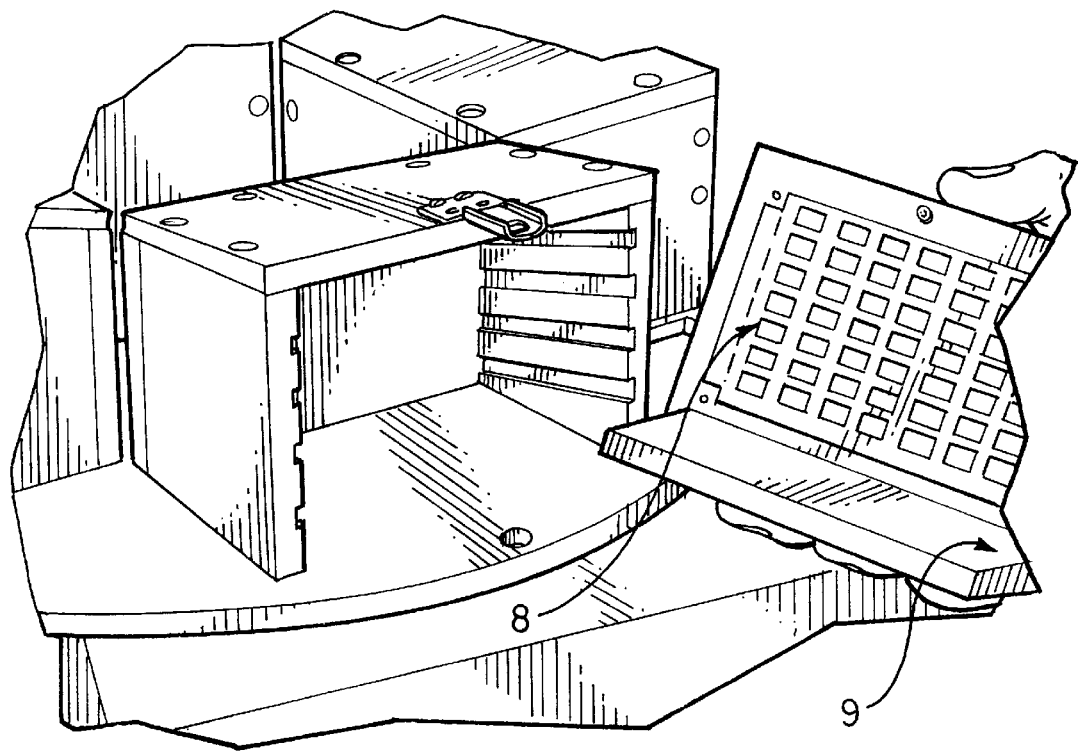
Figure 5A:
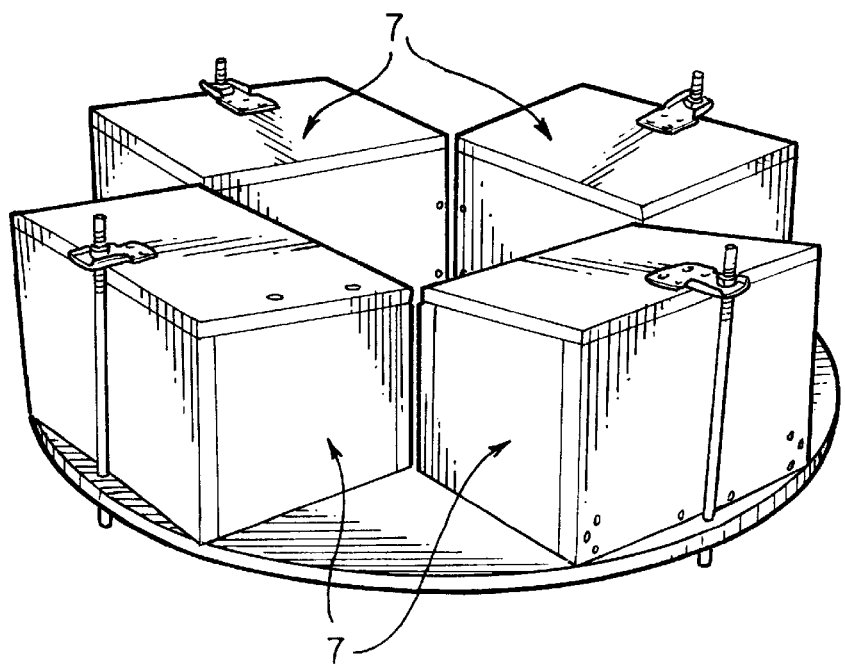
Figure 5C:
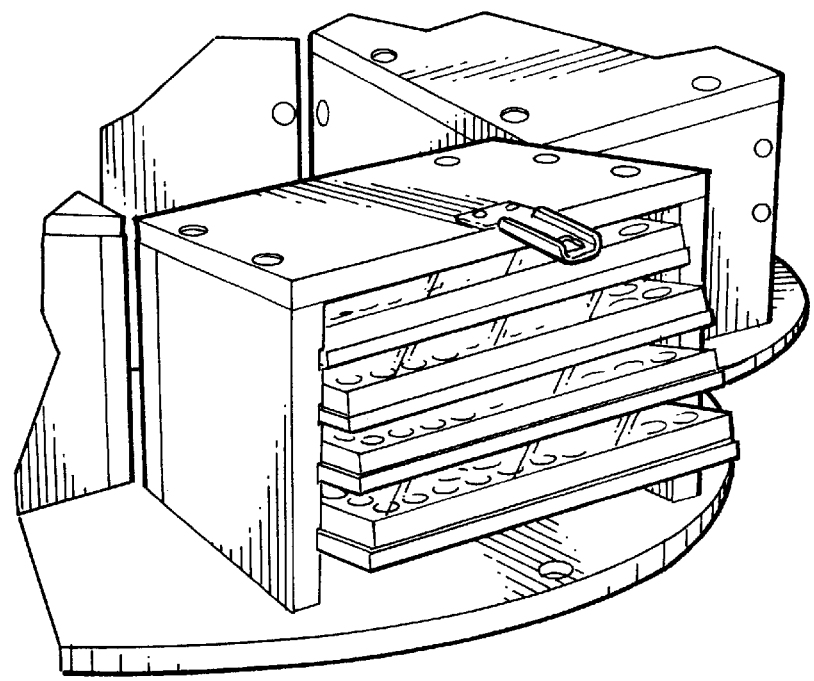
Figure 5D:
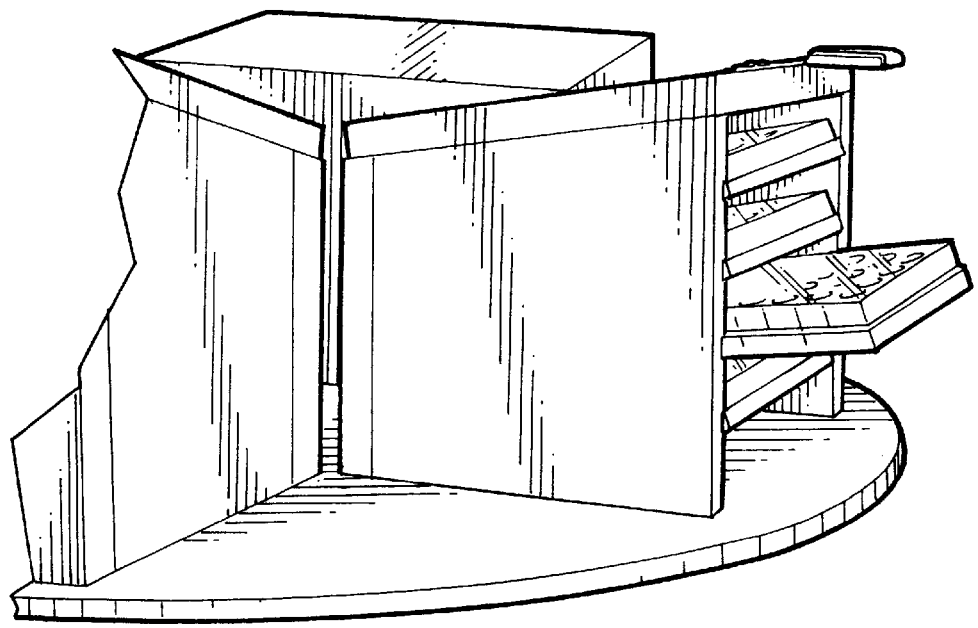

FIGS. 5A and B show a centrifuge rotor with four closed boxes (housings (7)) which can house four plates each. Closing of boxes is realized by a detachable retainer wall (8) with hollow "shoe" (9) in which the liquid removed during centrifugation resides after centrifugation stops. FIG. 5C shows four plates in the box and 5D illustrates the plate tilt.

FIGS. 9(A–C) illustrate a centrifuge built according to the present invention as a centrifuge-based solid phase synthetic apparatus. The system has an integrated 96 channel liquid distribution system. FIG. 9A shows a centrifuge useful as a solid phase synthesizer in which tilted plates are centrifuged. This centrifuge has a rotor of a diameter 25 cm, on the perimeter of which are placed eight microtiterplates in permanent tilt of 9 degrees. The centrifuge is integrated with a 96 channel liquid distributor which can deliver solvent or solution of reagent from six different bottles into the plate positioned under the needles of the distributor. FIG. 9B shows the rotor of the centrifuge and FIG. 9C shows the detail of the microtiterplate attachment to the rotor.

5.3. APPLICATIONS

The methods and apparatus of the present invention are advantageously useful for the manual or automated preparation of combinatorial libraries or megaarrays of compounds by solid phase organic synthesis. As is well known to those skilled in the art, such combinatorial libraries or megaarrays have numerous uses, in particular, for the selection of pharmaceutical lead compounds, for the optimization of pharmaceutical lead compounds and for the identification and/or isolation of pharmaceutical drugs. The methods and apparatus of the invention for liquid/solid phase separation can also advantageously be used for applications in analytical chemistry, biochemistry, screening libraries etc.

The invention is further described by way of the following illustrative examples which are in no way intended to limit the scope of the invention.

6. EXAMPLE

Removal of Liquid Phase Without Transfer of Solid Phase

A slurry of a solid phase support, i.e., 3 mg of resin beads in 100 $\mu$l of dimethylformamide (DMF), was distributed into a row (row H) of wells of a standard polypropylene microtiter plate. All other rows of wells of the microtiter plate were left empty. The microtiter plate was placed on the perimeter of a rotor, of a centrifuge, attached to a stepper motor using a holding plate. The radius of the centrifuge rotor was 20 cm. The swivel of the holding plate was adjusted so that the tilt could not reach more than about 9 degrees. The rotor was rotated at a speed of 350 rpms. All the liquid phase was expelled from the wells originally containing the slurry.

After an initial centrifugal removal of the liquid phase from the microtiter plate wells, the process of adding a solvent to certain wells of row H and removing the liquid phase centrifugally was repeated twenty times and a dissecting microscope was used to verify the removal of liquid phase.

Figure 8B:
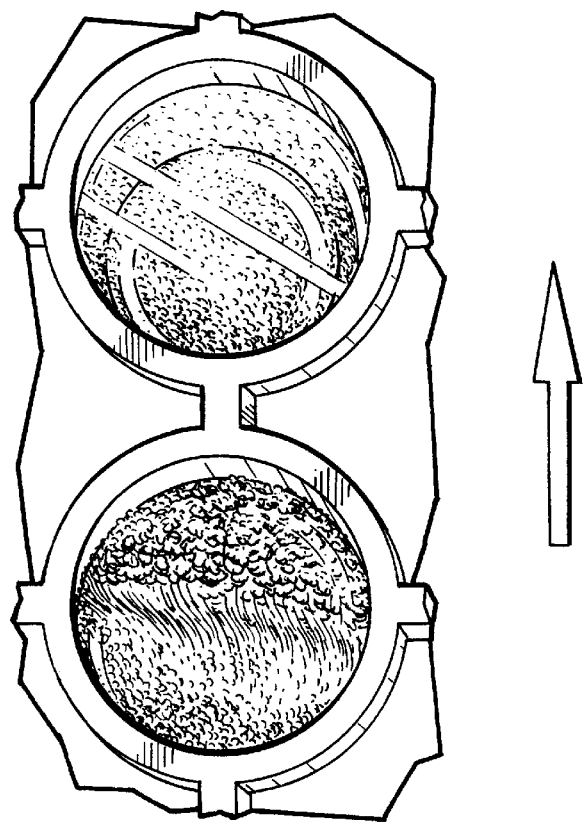
Figure 8A:
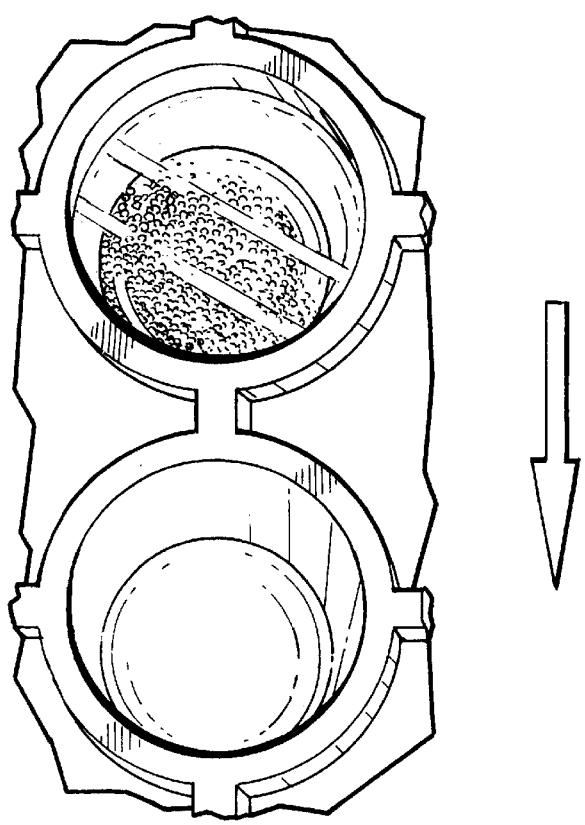
Figure 8D:
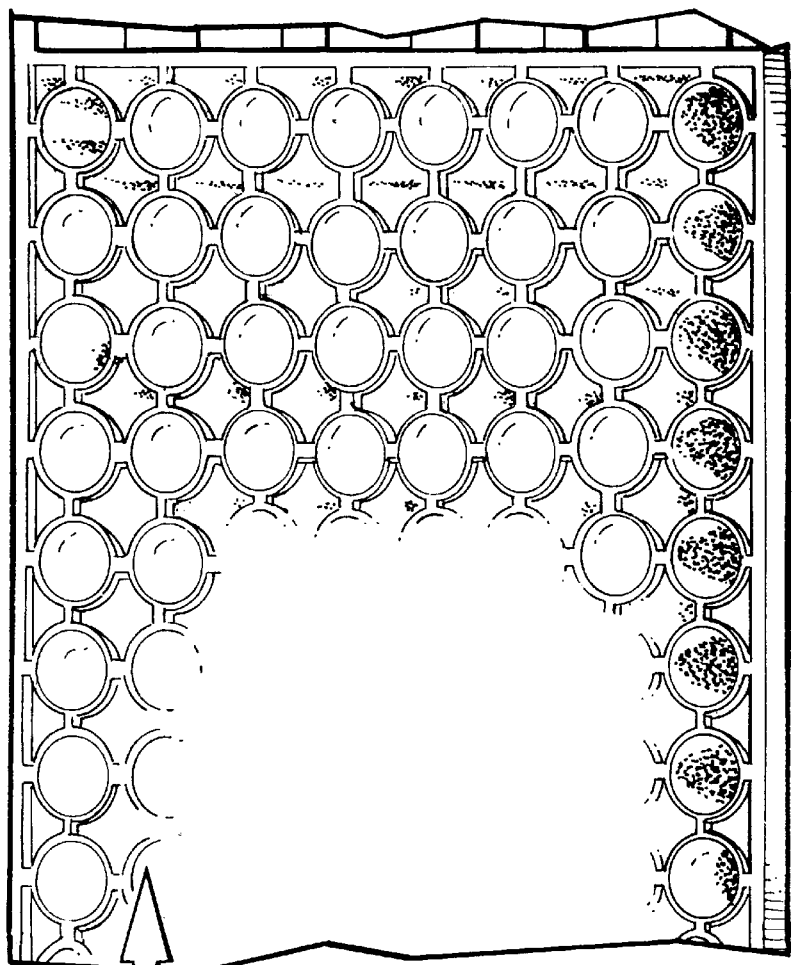

FIG. 8A demonstrates that there was no transfer of solid phase, i.e., resin particles, from the wells originally containing the slurry of solid phase supports to the originally empty wells although the liquid phase was removed from the wells, even when the empty wells were positioned on the outer perimeter of the rotor and the originally "filled" wells were positioned closer to the center of rotation.

FIG. 8B illustrates the same experiment in which the only difference was the amount of resin (12 mg) placed in individual wells. Even though the pocket could not retain all the resin during centrifugation, none of the resin beads was transferred to an adjacent well. The resin landed in the "inter-well" space.

Figure 8C:
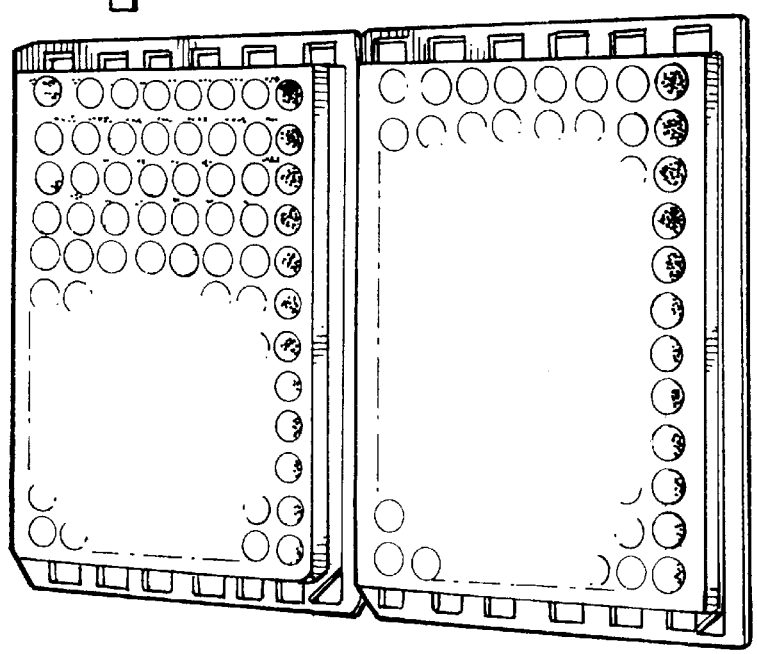

FIG. 8C further illustrates the situation when the pocket could not retain all the resin. In another experiment, the plate was loaded by resin only in the first row and the amounts of the resin were different in each well (from the left: 1, 1, 2, 2, 3, 3, 4, 5, 6, 7, 8, 9 mg). The trailings of resin from wells loaded with more than 5 mg are clearly visible in the detailed picture, however, even in this case there were no beads found inside of any other well but the wells in the first row.

7. EXAMPLE

Synthesis of an Array of 380 Tetrahydroisoouinolinones

The following example illustrates the use of the apparatus and method for separation of liquid and solid in on solid phase synthesis.

Four shallow well microtiter plates were filled with Tenta-Gel S-RAM resin (100–200 mesh, 0.24 mmol/g, Rapp Polymere, Tubingen, Germany) 3 mg per well, DMF slurry, distributed by a 12 channel pipettor. Microtiter plates were placed on the centrifuge rotor in a tilted position (9 degree tilt) and solvent was removed by centrifugation at 350 rpm. Prior to the distribution, the resin was colorized by the addition of bromophenol blue solution (5 drops of 0.1% solution). Solutions of Fmoc protected amino acids (see Table 1 for amino acids used) in dimethylformamide (50 µl of 0.2M solution) containing N-hydroxybenzotriazole (0.2M) were delivered into individual wells of the microtiter plate by 8 channel pipettor. Diisopropylcarbodiimide was added into the amino acid solution to form 0.2M solution just prior to the distribution into the wells.

TABLE 1

List of synthesized compounds
(A is Plate Number)
(R3 is always Aminoethylpyrrolidine)

| A | WELL | R1: AMINO ACIDS | R2: ALDEHYDE |
|---|---|---|---|
| 1 | A1 | Gly | Benzaldehyde |
| 1 | B1 | Gly | 1,4-Benzodioxan-6-carboxaldehyde |
| 1 | C1 | Gly | 1-Methylindole-3-carboxaldehyde |
| 1 | D1 | Gly | 2,3-Difluorobenzaldehyde |
| 1 | E1 | Gly | 2-Bromobenzaldehyde |
| 1 | F1 | Gly | 2-Chloro-5-nitrobenzaldehyde |
| 1 | G1 | Gly | 2-Furaldehyde |
| 1 | H1 | Gly | 2-Imidazolecarboxaldehyde |
| 1 | A2 | Gly | 2-Naphthaldehyde |
| 1 | B2 | Gly | 2-Pyridinecarboxaldehyde |
| 1 | C2 | Gly | 2-Thiophenecarboxaldehyde |
| 1 | D2 | Gly | 3,4-Dichlorobenzaldehyde |
| 1 | E2 | Gly | 3,5-Bis(trifluoromethyl)benzaldehyde |
| 1 | F2 | Gly | 3,5-Dihydroxybenzaldehyde |
| 1 | G2 | Gly | 3,5-Dimethoxybenzaldehyde |
| 1 | H2 | Gly | 3,5-Dimethyl-4-hydroxybenzaldehyde |
| 1 | A3 | Gly | 3-(4-Methoxyphenoxy)benzaldehyde |
| 1 | B3 | Gly | 3-Furaldehyde |
| 1 | C3 | Gly | 3-Hydroxybenzaldehyde |
| 1 | D3 | Gly | 3-Methyl-4-methoxybenzaldehyde |
| 1 | E3 | Gly | 3-Methylbenzaldehyde |
| 1 | F3 | Gly | 3-Nitrobenzaldehyde |
| 1 | G3 | Gly | 3-Pyridinecarboxaldehyde |
| 1 | H3 | Gly | 3-Thiophenecarboxaldehyde |
| 1 | A4 | Gly | 4-(3-Dimethylaminopropoxy)benzaldehyde |
| 1 | B4 | Gly | 4-(Dimethylamino)benzaldehyde |
| 1 | C4 | Gly | 4-(Methylthio)benzaldehyde |
| 1 | D4 | Gly | 4-(Trifluoromethyl)benzaldehyde |
| 1 | E4 | Gly | 4-Biphenylcarboxaldehyde |
| 1 | F4 | Gly | 4-Bromo-2-thiophenecarboxaldehyde |
| 1 | G4 | Gly | 4-Cyanobenzaldehyde |
| 1 | H4 | Gly | 4-Methoxy-1-naphthaldehyde |
| 1 | A5 | Gly | 4-Nitrobenzaldehyde |
| 1 | B5 | Gly | 4-Pyridinecarboxaldehyde |
| 1 | C5 | Gly | 5-(Hydroxymethyl)-2-furaldehyde |
| 1 | D5 | Gly | 5-Bromo-4-hydroxy-3-methoxybenzaldehyde |
| 1 | E5 | Gly | 5-Nitro-2-furaldehyde |
| 1 | F5 | Gly | 6-Methyl-2-pyridinecarboxaldehyde |
| 1 | G5 | 3-Aminopropionic | Benzaldehyde |
| 1 | H5 | 3-Aminopropionic | 1,4-Benzodioxan-6-carboxaldehyde |
| 1 | A6 | 3-Aminopropionic | 1-Methylindole-3-carboxaldehyde |
| 1 | B6 | 3-Aminopropionic | 2,3-Difluorobenzaldehyde |
| 1 | C6 | 3-Aminopropionic | 2-Bromobenzaldehyde |
| 1 | D6 | 3-Aminopropionic | 2-Chloro-5-nitrobenzaldehyde |
| 1 | E6 | 3-Aminopropionic | 2-Furaldehyde |
| 1 | F6 | 3-Aminopropionic | 2-Imidazolecarboxaldehyde |
| 1 | G6 | 3-Aminopropionic | 2-Naphthaldehyde |
| 1 | H6 | 3-Aminopropionic | 2-Pyridinecarboxaldehyde |
| 1 | A7 | 3-Aminopropionic | 2-Thiophenecarboxaldehyde |
| 1 | B7 | 3-Aminopropionic | 3,4-Dichlorobenzaldehyde |
| 1 | C7 | 3-Aminopropionic | 3,5-Bis(trifluoromethyl)benzaldehyde |
| 1 | D7 | 3-Aminopropionic | 3,5-Dihydroxybenzaldehyde |
| 1 | E7 | 3-Aminopropionic | 3,5-Dimethoxybenzaldehyde |
| 1 | F7 | 3-Aminopropionic | 3,5-Dimethyl-4-hydroxybenzaldehyde |
| 1 | G7 | 3-Aminopropionic | 3-(4-Methoxyphenoxy)benzaldehyde |
| 1 | H7 | 3-Aminopropionic | 3-Furaldehyde |
| 1 | A8 | 3-Aminopropionic | 3-Hydroxybenzaldehyde |

TABLE 1-continued

List of synthesized compounds
(A is Plate Number)
(R3 is always Aminoethylpyrrolidine)

| A | WELL | R1: AMINO ACIDS | R2: ALDEHYDE |
|---|------|-----------------|--------------|
| 1 | B8 | 3-Aminopropionic | 3-Methyl-4-methoxybenzaldehyde |
| 1 | C8 | 3-Aminopropionic | 3-Methylbenzaldehyde |
| 1 | D8 | 3-Aminopropionic | 3-Nitrobenzaldehyde |
| 1 | E8 | 3-Aminopropionic | 3-Pyridinecarboxaldehyde |
| 1 | F8 | 3-Aminopropionic | 3-Thiophenecarboxaldehyde |
| 1 | G8 | 3-Aminopropionic | 4-(3-Dimethylaminopropoxy)benzaldehyde |
| 1 | H8 | 3-Aminopropionic | 4-(Dimethylamino)benzaldehyde |
| 1 | A9 | 3-Aminopropionic | 4-(Methylthio)benzaldehyde |
| 1 | B9 | 3-Aminopropionic | 4-(Trifluoromethyl)benzaldehyde |
| 1 | C9 | 3-Aminopropionic | 4-Biphenylcarboxaldehyde |
| 1 | D9 | 3-Aminopropionic | 4-Bromo-2-thiophenecarboxaldehyde |
| 1 | E9 | 3-Aminopropionic | 4-Cyanobenzaldehyde |
| 1 | F9 | 3-Aminopropionic | 4-Methoxy-1-naphthaldehyde |
| 1 | G9 | 3-Aminopropionic | 4-Nitrobenzaldehyde |
| 1 | H9 | 3-Aminopropionic | 4-Pyridinecarboxaldehyde |
| 1 | A10 | 3-Aminopropionic | 5-(Hydroxymethyl)-2-furaldehyde |
| 1 | B10 | 3-Aminopropionic | 5-Bromo-4-hydroxy-3-methoxybenzaldehyde |
| 1 | C10 | 3-Aminopropionic | 5-Nitro-2-furaldehyde |
| 1 | D10 | 3-Aminopropionic | 6-Methyl-2-pyridinecarboxaldehyde |
| 1 | E10 | 5-Aminopentanoic | Benzaldehyde |
| 1 | F10 | 5-Aminopentanoic | 1,4-Benzodioxan-6-carboxaldehyde |
| 1 | G10 | 5-Aminopentanoic | 1-Methylindole-3-carboxaldehyde |
| 1 | H10 | 5-Aminopentanoic | 2,3-Difluorobenzaldehyde |
| 1 | A11 | 5-Aminopentanoic | 2-Bromobenzaldehyde |
| 1 | B11 | 5-Aminopentanoic | 2-Chloro-5-nitrobenzaldehyde |
| 1 | C11 | 5-Aminopentanoic | 2-Furaldehyde |
| 1 | D11 | 5-Aminopentanoic | 2-Imidazolecarboxaldehyde |
| 1 | E11 | 5-Aminopentanoic | 2-Naphthaldehyde |
| 1 | F11 | 5-Aminopentanoic | 2-Pyridinecarboxaldehyde |
| 1 | G11 | 5-Aminopentanoic | 2-Thiophenecarboxaldehyde |
| 1 | H11 | 5-Aminopentanoic | 3,4-Dichlorobenzaldehyde |
| 1 | A12 | 5-Aminopentanoic | 3,5-Bis(trifluoromethyl)benzaldehyde |
| 1 | B12 | 5-Aminopentanoic | 3,5-Dihydroxybenzaldehyde |
| 1 | C12 | 5-Aminopentanoic | 3,5-Dimethoxybenzaldehyde |
| 1 | D12 | 5-Aminopentanoic | 3,5-Dimethyl-4-hydroxybenzaldehyde |
| 1 | E12 | 5-Aminopentanoic | 3-(4-Methoxyphenoxy)benzaldehyde |
| 1 | F12 | 5-Aminopentanoic | 3-Furaldehyde |
| 1 | G12 | 5-Aminopentanoic | 3-Hydroxybenzaldehyde |
| 1 | H12 | 5-Aminopentanoic | 3-Methyl-4-methoxybenzaldehyde |
| 2 | A1 | 5-Aminopentanoic | 3-Methylbenzaldehyde |
| 2 | B1 | 5-Aminopentanoic | 3-Nitrobenzaldehyde |
| 2 | C1 | 5-Aminopentanoic | 3-Pyridinecarboxaldehyde |
| 2 | D1 | 5-Aminopentanoic | 3-Thiophenecarboxaldehyde |
| 2 | E1 | 5-Aminopentanoic | 4-(3-Dimethylaminopropoxy)benzaldehyde |
| 2 | F1 | 5-Aminopentanoic | 4-(Dimethylamino)benzaldehyde |
| 2 | G1 | 5-Aminopentanoic | 4-(Methylthio)benzaldehyde |
| 2 | H1 | 5-Aminopentanoic | 4-(Trifluoromethyl)benzaldehyde |
| 2 | A2 | 5-Aminopentanoic | 4-Biphenylcarboxaldehyde |
| 2 | B2 | 5-Aminopentanoic | 4-Bromo-2-thiophenecarboxaldehyde |
| 2 | C2 | 5-Aminopentanoic | 4-Cyanobenzaldehyde |
| 2 | D2 | 5-Aminopentanoic | 4-Methoxy-1-naphthaldehyde |
| 2 | E2 | 5-Aminopentanoic | 4-Nitrobenzaldehyde |
| 2 | F2 | 5-Aminopentanoic | 4-Pyridinecarboxaldehyde |
| 2 | G2 | 5-Aminopentanoic | 5-(Hydroxymethyl)-2-furaldehyde |
| 2 | H2 | 5-Aminopentanoic | 5-Bromo-4-hydroxy-3-methoxybenzaldehyde |
| 2 | A3 | 5-Aminopentanoic | 5-Nitro-2-furaldehyde |
| 2 | B3 | 5-Aminopentanoic | 6-Methyl-2-pyridinecarboxaldehyde |
| 2 | C3 | 7-Aminoheptanoic | Benzaldehyde |
| 2 | D3 | 7-Aminoheptanoic | 1,4-Benzodioxan-6-carboxaldehyde |
| 2 | E3 | 7-Aminoheptanoic | 1-Methylindole-3-carboxaldehyde |
| 2 | F3 | 7-Aminoheptanoic | 2,3-Difluorobenzaldehyde |
| 2 | G3 | 7-Aminoheptanoic | 2-Bromobenzaldehyde |
| 2 | H3 | 7-Aminoheptanoic | 2-Chloro-5-nitrobenzaldehyde |
| 2 | A4 | 7-Aminoheptanoic | 2-Furaldehyde |
| 2 | B4 | 7-Aminoheptanoic | 2-Imidazolecarboxaldehyde |
| 2 | C4 | 7-Aminoheptanoic | 2-Naphthaldehyde |
| 2 | D4 | 7-Aminoheptanoic | 2-Pyridinecarboxaldehyde |
| 2 | E4 | 7-Aminoheptanoic | 2-Thiophenecarboxaldehyde |
| 2 | F4 | 7-Aminoheptanoic | 3,4-Dichlorobenzaldehyde |
| 2 | G4 | 7-Aminoheptanoic | 3,5-Bis(trifluoromethyl)benzaldehyde |
| 2 | H4 | 7-Aminoheptanoic | 3,5-Dihydroxybenzaldehyde |
| 2 | A5 | 7-Aminoheptanoic | 3,5-Dimethoxybenzaldehyde |
| 2 | B5 | 7-Aminoheptanoic | 3,5-Dimethyl-4-hydroxybenzaldehyde |

TABLE 1-continued

List of synthesized compounds
(A is Plate Number)
(R3 is always Aminoethylpyrrolidine)

| A | WELL | R1: AMINO ACIDS | R2: ALDEHYDE |
|---|---|---|---|
| 2 | C5 | 7-Aminoheptanoic | 3-(4-Methoxyphenoxy)benzaldehyde |
| 2 | D5 | 7-Aminoheptanoic | 3-Furaldehyde |
| 2 | E5 | 7-Aminoheptanoic | 3-Hydroxybenzaldehyde |
| 2 | F5 | 7-Aminoheptanoic | 3-Methyl-4-methoxybenzaldehyde |
| 2 | G5 | 7-Aminoheptanoic | 3-Methylbenzaldehyde |
| 2 | H5 | 7-Aminoheptanoic | 3-Nitrobenzaldehyde |
| 2 | A6 | 7-Aminoheptanoic | 3-Pyridinecarboxaldehyde |
| 2 | B6 | 7-Aminoheptanoic | 3-Thiophenecarboxaldehyde |
| 2 | C6 | 7-Aminoheptanoic | 4-(3-Dimethylaminopropoxy)benzaldehyde |
| 2 | D6 | 7-Aminoheptanoic | 4-(Dimethylamino)benzaldehyde |
| 2 | E6 | 7-Aminoheptanoic | 4-(Methylthio)benzaldehyde |
| 2 | F6 | 7-Aminoheptanoic | 4-(Trifluoromethyl)benzaldehyde |
| 2 | G6 | 7-Aminoheptanoic | 4-Biphenylcarboxaldehyde |
| 2 | H6 | 7-Aminoheptanoic | 4-Bromo-2-thiophenecarboxaldehyde |
| 2 | A7 | 7-Aminoheptanoic | 4-Cyanobenzaldehyde |
| 2 | B7 | 7-Aminoheptanoic | 4-Methoxy-1-naphthaldehyde |
| 2 | C7 | 7-Aminoheptanoic | 4-Nitrobenzaldehyde |
| 2 | D7 | 7-Aminoheptanoic | 4-Pyridinecarboxaldehyde |
| 2 | E7 | 7-Aminoheptanoic | 5-(Hydroxymethyl)-2-furaldehyde |
| 2 | F7 | 7-Aminoheptanoic | 5-Bromo-4-hydroxy-3-methoxybenzaldehyde |
| 2 | G7 | 7-Aminoheptanoic | 5-Nitro-2-furaldehyde |
| 2 | H7 | 7-Aminoheptanoic | 6-Methyl-2-pyridinecarboxaldehyde |
| 2 | A8 | Dap | Benzaldehyde |
| 2 | B8 | Dap | 1,4-Benzodioxan-6-carboxaldehyde |
| 2 | C8 | Dap | 1-Methylindole-3-carboxaldehyde |
| 2 | D8 | Dap | 2,3-Difluorobenzaldehyde |
| 2 | E8 | Dap | 2-Bromobenzaldehyde |
| 2 | F8 | Dap | 2-Chloro-5-nitrobenzaldehyde |
| 2 | G8 | Dap | 2-Furaldehyde |
| 2 | H8 | Dap | 2-Imidazolecarboxaldehyde |
| 2 | A9 | Dap | 2-Naphthaldehyde |
| 2 | B9 | Dap | 2-Pyridinecarboxaldehyde |
| 2 | C9 | Dap | 2-Thiophenecarboxaldehyde |
| 2 | D9 | Dap | 3,4-Dichlorobenzaldehyde |
| 2 | E9 | Dap | 3,5-Bis(trifluoromethyl)benzaldehyde |
| 2 | F9 | Dap | 3,5-Dihydroxybenzaldehyde |
| 2 | G9 | Dap | 3,5-Dimethoxybenzaldehyde |
| 2 | H9 | Dap | 3,5-Dimethyl-4-hydroxybenzaldehyde |
| 2 | A10 | Dap | 3-(4-Methoxyphenoxy)benzaldehyde |
| 2 | B10 | Dap | 3-Furaldehyde |
| 2 | C10 | Dap | 3-Hydroxybenzaldehyde |
| 2 | D10 | Dap | 3-Methyl-4-methoxybenzaldehyde |
| 2 | E10 | Dap | 3-Methylbenzaldehyde |
| 2 | F10 | Dap | 3-Nitrobenzaldehyde |
| 2 | G10 | Dap | 3-Pyridinecarboxaldehyde |
| 2 | H10 | Dap | 3-Thiophenecarboxaldehyde |
| 2 | A11 | Dap | 4-(3-Dimethylaminopropoxy)benzaldehyde |
| 2 | B11 | Dap | 4-(Dimethylamino)benzaldehyde |
| 2 | C11 | Dap | 4-(Methylthio)benzaldehyde |
| 2 | D11 | Dap | 4-(Trifluoromethyl)benzaldehyde |
| 2 | E11 | Dap | 4-Biphenylcarboxaldehyde |
| 2 | F11 | Dap | 4-Bromo-2-thiophenecarboxaldehyde |
| 2 | G11 | Dap | 4-Cyanobenzaldehyde |
| 2 | H11 | Dap | 4-Methoxy-1-naphthaldehyde |
| 2 | A12 | Dap | 4-Nitrobenzaldehyde |
| 2 | B12 | Dap | 4-Pyridinecarboxaldehyde |
| 2 | C12 | Dap | 5-(Hydroxymethyl)-2-furaldehyde |
| 2 | D12 | Dap | 5-Bromo-4-hydroxy-3-methoxybenzaldehyde |
| 2 | E12 | Dap | 5-Nitro-2-furaldehyde |
| 2 | F12 | Dap | 6-Methyl-2-pyridinecarboxaldehyde |
| 2 | G12 | Lys | Benzaldehyde |
| 2 | H12 | Lys | 1,4-Benzodioxan-6-carboxaldehyde |
| 3 | A1 | Lys | 1-Methylindole-3-carboxaldehyde |
| 3 | B1 | Lys | 2,3-Difluorobenzaldehyde |
| 3 | C1 | Lys | 2-Bromobenzaldehyde |
| 3 | D1 | Lys | 2-Chloro-5-nitrobenzaldehyde |
| 3 | E1 | Lys | 2-Furaldehyde |
| 3 | F1 | Lys | 2-Imidazolecarboxaldehyde |
| 3 | G1 | Lys | 2-Naphthaldehyde |
| 3 | H1 | Lys | 2-Pyridinecarboxaldehyde |
| 3 | A2 | Lys | 2-Thiophenecarboxaldehyde |
| 3 | B2 | Lys | 3,4-Dichlorobenzaldehyde |
| 3 | C2 | Lys | 3,5-Bis(trifluoromethyl)benzaldehyde |

TABLE 1-continued

List of synthesized compounds
(A is Plate Number)
(R3 is always Aminoethylpyrrolidine)

| A | WELL | R1: AMINO ACIDS | R2: ALDEHYDE |
|---|---|---|---|
| 3 | D2 | Lys | 3,5-Dihydroxybenzaldehyde |
| 3 | E2 | Lys | 3,5-Dimethoxybenzaldehyde |
| 3 | F2 | Lys | 3,5-Dimethyl-4-hydroxybenzaldehyde |
| 3 | G2 | Lys | 3-(4-Methoxyphenoxy)benzaldehyde |
| 3 | H2 | Lys | 3-Furaldehyde |
| 3 | A3 | Lys | 3-Hydroxybenzaldehyde |
| 3 | B3 | Lys | 3-Methyl-4-methoxybenzaldehyde |
| 3 | C3 | Lys | 3-Methylbenzaldehyde |
| 3 | D3 | Lys | 3-Nitrobenzaldehyde |
| 3 | E3 | Lys | 3-Pyridinecarboxaldehyde |
| 3 | F3 | Lys | 3-Thiophenecarboxaldehyde |
| 3 | G3 | Lys | 4-(3-Dimethylaminopropoxy)benzaldehyde |
| 3 | H3 | Lys | 4-(Dimethylamino)benzaldehyde |
| 3 | A4 | Lys | 4-(Methylthio)benzaldehyde |
| 3 | B4 | Lys | 4-(Trifluoromethyl)benzaldehyde |
| 3 | C4 | Lys | 4-Biphenylcarboxaldehyde |
| 3 | D4 | Lys | 4-Bromo-2-thiophenecarboxaldehyde |
| 3 | E4 | Lys | 4-Cyanobenzaldehyde |
| 3 | F4 | Lys | 4-Methoxy-1-naphthaldehyde |
| 3 | G4 | Lys | 4-Nitrobenzaldehyde |
| 3 | H4 | Lys | 4-Pyridinecarboxaldehyde |
| 3 | A5 | Lys | 5-(Hydroxymethyl)-2-furaldehyde |
| 3 | B5 | Lys | 5-Bromo-4-hydroxy-3-methoxybenzaldehyde |
| 3 | C5 | Lys | 5-Nitro-2-furaldehyde |
| 3 | D5 | Lys | 6-Methyl-2-pyridinecarboxaldehyde |
| 3 | E5 | (S/R)-3-Amino-2-methyl-propionic | Benzaldehyde |
| 3 | F5 | (S/R)-3-Amino-2-methyl-propionic | 1,4-Benzodioxan-6-carboxaldehyde |
| 3 | G5 | (S/R)-3-Amino-2-methyl-propionic | 1-Methylindole-3-carboxaldehyde |
| 3 | H5 | (S/R)-3-Amino-2-methyl-propionic | 2,3-Difluorobenzaldehyde |
| 3 | A6 | (S/R)-3-Amino-2-methyl-propionic | 2-Bromobenzaldehyde |
| 3 | B6 | (S/R)-3-Amino-2-methyl-propionic | 2-Chloro-5-nitrobenzaldehyde |
| 3 | C6 | (S/R)-3-Amino-2-methyl-propionic | 2-Furaldehyde |
| 3 | D6 | (S/R)-3-Amino-2-methyl-propionic | 2-Imidazolecarboxaldehyde |
| 3 | E6 | (S/R)-3-Amino-2-methyl-propionic | 2-Naphthaldehyde |
| 3 | F6 | (S/R)-3-Amino-2-methyl-propionic | 2-Pyridinecarboxaldehyde |
| 3 | G6 | (S/R)-3-Amino-2-methyl-propionic | 2-Thiophenecarboxaldehyde |
| 3 | H6 | (S/R)-3-Amino-2-methyl-propionic | 3,4-Dichlorobenzaldehyde |
| 3 | A7 | (S/R)-3-Amino-2-methyl-propionic | 3,5-Bis(trifluoromethyl)benzaldehyde |
| 3 | B7 | (S/R)-3-Amino-2-methyl-propionic | 3,5-Dihydroxybenzaldehyde |
| 3 | C7 | (S/R)-3-Amino-2-methyl-propionic | 3,5-Dimethoxybenzaldehyde |
| 3 | D7 | (S/R)-3-Amino-2-methyl-propionic | 3,5-Dimethyl-4-hydroxybenzaldehyde |
| 3 | E7 | (S/R)-3-Amino-2-methyl-propionic | 3-(4-Methoxyphenoxy)benzaldehyde |
| 3 | F7 | (S/R)-3-Amino-2-methyl-propionic | 3-Furaldehyde |
| 3 | G7 | (S/R)-3-Amino-2-methyl-propionic | 3-Hydroxybenzaldehyde |
| 3 | H7 | (S/R)-3-Amino-2-methyl-propionic | 3-Methyl-4-methoxybenzaldehyde |
| 3 | A8 | (S/R)-3-Amino-2-methyl-propionic | 3-Methylbenzaldehyde (m- Tolualdehyde) |
| 3 | B8 | (S/R)-3-Amino-2-methyl-propionic | 3-Nitrobenzaldehyde |
| 3 | C8 | (S/R)-3-Amino-2-methyl-propionic | 3-Pyridinecarboxaldehyde |
| 3 | D8 | (S/R)-3-Amino-2-methyl-propionic | 3-Thiophenecarboxaldehyde |

TABLE 1-continued

List of synthesized compounds
(A is Plate Number)
(R3 is always Aminoethylpyrrolidine)

| A | WELL | R1: AMINO ACIDS | R2: ALDEHYDE |
|---|---|---|---|
| 3 | E8 | (S/R)-3-Amino-2-methyl-propionic | 4-(3-Dimethylaminopropoxy)benzaldehyde |
| 3 | F8 | (S/R)-3-Amino-2-methyl-propionic | 4-(Dimethylamino)benzaldehyde |
| 3 | G8 | (S/R)-3-Amino-2-methyl-propionic | 4-(Methylthio)benzaldehyde |
| 3 | H8 | (S/R)-3-Amino-2-methyl-propionic | 4-(Trifluoromethyl)benzaldehyde |
| 3 | A9 | (S/R)-3-Amino-2-methyl-propionic | 4-Biphenylcarboxaldehyde |
| 3 | B9 | (S/R)-3-Amino-2-methyl-propionic | 4-Bromo-2-thiophenecarboxaldehyde |
| 3 | C9 | (S/R)-3-Amino-2-methyl-propionic | 4-Cyanobenzaldehyde |
| 3 | D9 | (S/R)-3-Amino-2-methyl-propionic | 4-Methoxy-1-naphthaldehyde |
| 3 | E9 | (S/R)-3-Amino-2-methyl-propionic | 4-Nitrobenzaldehyde |
| 3 | F9 | (S/R)-3-Amino-2-methyl-propionic | 4-Pyridinecarboxaldehyde |
| 3 | G9 | (S/R)-3-Amino-2-methyl-propionic | 5-(Hydroxymethyl)-2-furaldehyde |
| 3 | H9 | (S/R)-3-Amino-2-methyl-propionic | 5-Bromo-4-hydroxy-3-methoxybenzaldehyde |
| 3 | A10 | (S/R)-3-Amino-2-methyl-propionic | 5-Nitro-2-furaldehyde |
| 3 | B10 | (S/R)-3-Amino-2-methyl-propionic | 6-Methyl-2-pyridinecarboxaldehyde |
| 3 | C10 | 2-(2-Aminoethoxy)acetic | Benzaldehyde |
| 3 | D10 | 2-(2-Aminoethoxy)acetic | 1,4-Benzodioxan-6-carboxaldehyde |
| 3 | E10 | 2-(2-Aminoethoxy)acetic | 1-Methylindole-3-carboxaldehyde |
| 3 | F10 | 2-(2-Aminoethoxy)acetic | 2,3-Difluorobenzaldehyde |
| 3 | G10 | 2-(2-Aminoethoxy)acetic | 2-Bromobenzaldehyde |
| 3 | H10 | 2-(2-Aminoethoxy)acetic | 2-chloro-5-nitrobenzaldehyde |
| 3 | A11 | 2-(2-Aminoethoxy)acetic | 2-Furaldehyde |
| 3 | B11 | 2-(2-Aminoethoxy)acetic | 2-Imidazolecarboxaldehyde |
| 3 | C11 | 2-(2-Aminoethoxy)acetic | 2-Naphthaldehyde |
| 3 | D11 | 2-(2-Aminoethoxy)acetic | 2-Pyridinecarboxaldehyde |
| 3 | E11 | 2-(2-Aminoethoxy)acetic | 2-Thiophenecarboxaldehyde |
| 3 | F11 | 2-(2-Aminoethoxy)acetic | 3,4-Dichlorobenzaldehyde |
| 3 | G11 | 2-(2-Aminoethoxy)acetic | 3,5-Bis(trifluoromethyl)benzaldehyde |
| 3 | H11 | 2-(2-Aminoethoxy)acetic | 3,5-Dihydroxybenzaldehyde |
| 3 | A12 | 2-(2-Aminoethoxy)acetic | 3,5-Dimethoxybenzaldehyde |
| 3 | B12 | 2-(2-Aminoethoxy)acetic | 3,5-Dimethyl-4-hydroxybenzaldehyde |
| 3 | C12 | 2-(2-Aminoethoxy)acetic | 3-(4-Methoxyphenoxy)benzaldehyde |
| 3 | D12 | 2-(2-Aminoethoxy)acetic | 3-Furaldehyde |
| 3 | E12 | 2-(2-Aminoethoxy)acetic | 3-Hydroxybenzaldehyde |
| 3 | F12 | 2-(2-Aminoethoxy)acetic | 3-Methyl-4-methoxybenzaldehyde |
| 3 | G12 | 2-(2-Aminoethoxy)acetic | 3-Methylbenzaldehyde(m-Tolualdehyde) |
| 3 | H12 | 2-(2-Aminoethoxy)acetic | 3-Nitrobenzaldehyde |
| 4 | A1 | 2-(2-Aminoethoxy)acetic | 3-Pyridinecarboxaldehyde |
| 4 | B1 | 2-(2-Aminoethoxy)acetic | 3-Thiophenecarboxaldehyde |
| 4 | C1 | 2-(2-Aminoethoxy)acetic | 4-(3-Dimethylaminopropoxy)benzaldehyde |
| 4 | D1 | 2-(2-Aminoethoxy)acetic | 4-(Dimethylamino)benzaldehyde |
| 4 | E1 | 2-(2-Aminoethoxy)acetic | 4-(Methylthio)benzaldehyde |
| 4 | F1 | 2-(2-Aminoethoxy)acetic | 4-(Trifluoromethyl)benzaldehyde |
| 4 | G1 | 2-(2-Aminoethoxy)acetic | 4-Biphenylcarboxaldehyde |
| 4 | H1 | 2-(2-Aminoethoxy)acetic | 4-Bromo-2-thiophenecarboxaldehyde |
| 4 | A2 | 2-(2-Aminoethoxy)acetic | 4-Cyanobenzaldehyde |
| 4 | B2 | 2-(2-Aminoethoxy)acetic | 4-Methoxy-1-naphthaldehyde |
| 4 | C2 | 2-(2-Aminoethoxy)acetic | 4-Nitrobenzaldehyde |
| 4 | D2 | 2-(2-Aminoethoxy)acetic | 4-Pyridinecarboxaldehyde |
| 4 | E2 | 2-(2-Aminoethoxy)acetic | 5-(Hydroxymethyl)-2-furaldehyde |
| 4 | F2 | 2-(2-Aminoethoxy)acetic | 5-Bromo-4-hydroxy-3-methoxybenzaldehyde |
| 4 | G2 | 2-(2-Aminoethoxy)acetic | 5-Nitro-2-furaldehyde |
| 4 | H2 | 2-(2-Aminoethoxy)acetic | 6-Methyl-2-pyridinecarboxaldehyde |
| 4 | A3 | trans-4-(Aminomethyl)cyclohexanecarboxylic | Benzaldehyde |
| 4 | B3 | trans-4-(Aminomethyl)cyclohexanecarboxylic | 1,4-Benzodioxan-6-carboxaldehyde |
| 4 | C3 | trans-4-(Aminomethyl)cyclohexanecarboxylic | 1-Methylindole-3-carboxaldehyde |

TABLE 1-continued

List of synthesized compounds
(A is Plate Number)
(R3 is always Aminoethylpyrrolidine)

| A | WELL | R1: AMINO ACIDS | R2: ALDEHYDE |
|---|---|---|---|
| 4 | D3 | trans-4-(Aminomethyl)cyclohexanecarboxylic | 2,3-Difluorobenzaldehyde |
| 4 | E3 | trans-4-(Aminomethyl)cyclohexanecarboxylic | 2-Bromobenzaldehyde |
| 4 | F3 | trans-4-(Aminomethyl)cyclohexanecarboxylic | 2-Chloro-5-nitrobenzaldehyde |
| 4 | G3 | trans-4-(Aminomethyl)cyclohexanecarboxylic | 2-Furaldehyde |
| 4 | H3 | trans-4-(Aminomethyl)cyclohexanecarboxylic | 2-Imidazolecarboxaldehyde |
| 4 | A4 | trans-4-(Aminomethyl)cyclohexanecarboxylic | 2-Naphthaldehyde |
| 4 | B4 | trans-4-(Aminomethyl)cyclohexanecarboxylic | 2-Pyridinecarboxaldehyde |
| 4 | C4 | trans-4-(Aminomethyl)cyclohexanecarboxylic | 2-Thiophenecarboxaldehyde |
| 4 | D4 | trans-4-(Aminomethyl)cyclohexanecarboxylic | 3,4-Dichlorobenzaldehyde |
| 4 | E4 | trans-4-(Aminomethyl)cyclohexanecarboxylic | 3,5-Bis(trifluoromethyl)benzaldehyde |
| 4 | F4 | trans-4-(Aminomethyl)cyclohexanecarboxylic | 3,5-Dihydroxybenzaldehyde |
| 4 | G4 | trans-4-(Aminomethyl)cyclohexanecarboxylic | 3,5-Dimethoxybenzaldehyde |
| 4 | H4 | trans-4-(Aminomethyl)cyclohexanecarboxylic | 3,5-Dimethyl-4-hydroxybenzaldehyde |
| 4 | A5 | trans-4-(Aminomethyl)cyclohexanecarboxylic | 3-(4-Methoxyphenoxy)benzaldehyde |
| 4 | B5 | trans-4-(Aminomethyl)cyclohexanecarboxylic | 3-Furaldehyde |
| 4 | C5 | trans-4-(Aminomethyl)cyclohexanecarboxylic | 3-Hydroxybenzaldehyde |
| 4 | D5 | trans-4-(Aminomethyl)cyclohexanecarboxylic | 3-Methyl-4-methoxybenzaldehyde |
| 4 | E5 | trans-4-(Aminomethyl)cyclohexanecarboxylic | 3-Methylbenzaldehyde |
| 4 | F5 | trans-4-(Aminomethyl)cyclohexanecarboxylic | 3-Nitrobenzaldehyde |
| 4 | G5 | trans-4-(Aminomethyl)cyclohexanecarboxylic | 3-Pyridinecarboxaldehyde |
| 4 | H5 | trans-4-(Aminomethyl)cyclohexanecarboxylic | 3-Thiophenecarboxaldehyde |
| 4 | A6 | trans-4-(Aminomethyl)cyclohexanecarboxylic | 4-(3-Dimethylaminopropoxy)benzaldehyde |
| 4 | B6 | trans-4-(Aminomethyl)cyclohexanecarboxylic | 4-(Dimethylamino)benzaldehyde |
| 4 | C6 | trans-4-(Aminomethyl)cyclohexanecarboxylic | 4-(Methylthio)benzaldehyde |
| 4 | D6 | trans-4-(Aminomethyl)cyclohexanecarboxylic | 4-(Trifluoromethyl)benzaldehyde |
| 4 | E6 | trans-4-(Aminomethyl)cyclohexanecarboxylic | 4-Biphenylcarboxaldehyde |
| 4 | F6 | trans-4-(Aminomethyl)cyclohexanecarboxylic | 4-Bromo-2-thiophenecarboxaldehyde |
| 4 | G6 | trans-4-(Aminomethyl)cyclohexanecarboxylic | 4-Cyanobenzaldehyde |
| 4 | H6 | trans-4-(Aminomethyl)cyclohexanecarboxylic | 4-Methoxy-1-naphthaldehyde |
| 4 | A7 | trans-4-(Aminomethyl)cyclohexanecarboxylic | 4-Nitrobenzaldehyde |
| 4 | B7 | trans-4-(Aminomethyl)cyclohexanecarboxylic | 4-Pyridinecarboxaldehyde |
| 4 | C7 | trans-4-(Aminomethyl)cyclohexanecarboxylic | 5-(Hydroxymethyl)-2-furaldehyde |
| 4 | D7 | trans-4-(Aminomethyl)cyclohexanecarboxylic | 5-Bromo-4-hydroxy-3-methoxybenzaldehyde |
| 4 | E7 | trans-4-(Aminomethyl)cyclohexanecarboxylic | 5-Nitro-2-furaldehyde |
| 4 | F7 | trans-4-(Aminomethyl)cyclohexanecarboxylic | 6-Methyl-2-pyridinecarboxaldehyde |
| 4 | G7 | 4-(Aminomethyl)benzoic | Benzaldehyde |
| 4 | H7 | 4-(Aminomethyl)benzoic | 14-Benzodioxan-6-carboxaldehyde |
| 4 | A8 | 4-(Aminomethyl)benzoic | 1-Methylindole-3-carboxaldehyde |

TABLE 1-continued

List of synthesized compounds
(A is Plate Number)
(R3 is always Aminoethylpyrrolidine)

| A | WELL | R1: AMINO ACIDS | R2: ALDEHYDE |
|---|---|---|---|
| 4 | B8 | 4-(Aminomethyl)benzoic | 2,3-Difluorobenzaldehyde |
| 4 | C8 | 4-(Aminomethyl)benzoic | 2-Bromobenzaldehyde |
| 4 | D8 | 4-(Aminomethyl)benzoic | 2-Chloro-5-nitrobenzaldehyde |
| 4 | E8 | 4-(Aminomethyl)benzoic | 2-Furaldehyde |
| 4 | F8 | 4-(Aminomethyl)benzoic | 2-Imidazolecarboxaldehyde |
| 4 | G8 | 4-(Aminomethyl)benzoic | 2-Naphthaldehyde |
| 4 | H8 | 4-(Aminomethyl)benzoic | 2-Pyridinecarboxaldehyde |
| 4 | A9 | 4-(Aminomethyl)benzoic | 2-Thiophenecarboxaldehyde |
| 4 | B9 | 4-(Aminomethyl)benzoic | 3,4-Dichlorobenzaldehyde |
| 4 | C9 | 4-(Aminomethyl)benzoic | 3,5-Bis(trifluoromethyl)benzaldehyde |
| 4 | D9 | 4-(Aminomethyl)benzoic | 3,5-Dihydroxybenzaldehyde |
| 4 | E9 | 4-(Aminomethyl)benzoic | 3,5-Dimethoxybenzaldehyde |
| 4 | F9 | 4-(Aminomethyl)benzoic | 3,5-Dimethyl-4-hydroxybenzaldehyde |
| 4 | G9 | 4-(Aminomethyl)benzoic | 3-(4-Methoxyphenoxy)benzaldehyde |
| 4 | H9 | 4-(Aminomethyl)benzoic | 3-Furaldehyde |
| 4 | A10 | 4-(Aminomethyl)benzoic | 3-Hydroxybenzaldehyde |
| 4 | B10 | 4-(Aminomethyl)benzoic | 3-Methyl-4-methoxybenzaldehyde |
| 4 | C10 | 4-(Aminomethyl)benzoic | 3-Methylbenzaldehyde(m- Tolualdehyde) |
| 4 | D10 | 4-(Aminomethyl)benzoic | 3-Nitrobenzaldehyde |
| 4 | E10 | 4-(Aminomethyl)benzoic | 3-Pyridinecarboxaldehyde |
| 4 | F10 | 4-(Aminomethyl)benzoic | 3-Thiophenecarboxaldehyde |
| 4 | G10 | 4-(Aminomethyl)benzoic | 4-(3-Dimethylaminopropoxy)benzaldehyde |
| 4 | H10 | 4-(Aminomethyl)benzoic | 4-(Dimethylamino)benzaldehyde |
| 4 | A11 | 4-(Aminomethyl)benzoic | 4-(Methylthio)benzaldehyde |
| 4 | B11 | 4-(Aminomethyl)benzoic | 4-(Trifluoromethyl)benzaldehyde |
| 4 | C11 | 4-(Aminomethyl)benzoic | 4-Biphenylcarboxaldehyde |
| 4 | D11 | 4-(Aminomethyl)benzoic | 4-Bromo-2-thiophenecarboxaldehyde |
| 4 | E11 | 4-(Aminomethyl)benzoic | 4-Cyanobenzaldehyde |
| 4 | F11 | 4-(Aminomethyl)benzoic | 4-Methoxy-1-naphthaldehyde |
| 4 | G11 | 4-(Aminomethyl)benzoic | 4-Nitrobenzaldehyde |
| 4 | H11 | 4-(Aminomethyl)benzoic | 4-Pyridinecarboxaldehyde |
| 4 | A12 | 4-(Aminomethyl)benzoic | 5-(Hydroxymethyl)-2-furaldehyde |
| 4 | B12 | 4-(Aminomethyl)benzoic | 5-Bromo-4-hydroxy-3-methoxybenzaldehyde |
| 4 | C12 | 4-(Aminomethyl)benzoic | 5-Nitro-2-furaldehyde |
| 4 | D12 | 4-(Aminomethyl)benzoic | 6-Methyl-2-pyridinecarboxaldehyde |

As used in Table 1, "Dap" refers to (S)2,3-Diamino propionic acid.

Microtiter plates were closed by the polypropylene mats and placed on the shaker. After 3 hours, the color in all wells disappeared (coupling was completed) and plates were uncapped and placed onto the centrifuge rotor. Solutions were removed by centrifugation and washing solvent (DMF, 75 μl) was added by multichannel pipettor. This washing step was repeated four times with DMF and the solution of 50% piperidine in DMF was added (50 μl). After 15 minutes of incubation the plates were centrifuged and washing cycle with DMF was repeated four times, followed by washing with 0.05 M (50 μl) trimethylorthoformiate (2×). Multititer plates were transferred to the table of a liquid handling robotic station Multiprobe 104 (Packard Canberra), and appropriate aldehyde solutions (50 μl, 0.5 M in DMF) were added by multichannel pipetting. Then solution of trimethylorthoformiate (50 μl, 1M in DMF) was added to all wells, plates were closed by polypropylene mat application and placed onto a shaker. After 3 hour incubation plates were placed onto the centrifuge, liquid was removed and two washes with 0.2M trimethylorthoformiate in DMF were performed. Solution of homophthalic anhydride (0.4M in DMF, 50 μl, diisopropylethylamine was added to this solution just prior to the addition to wells to make the concentration 0.03M) was added to each well and closed multititerplates were shaken overnight. Multititerplates were placed on the centrifuge, liquid was removed and five washes with DMF were performed. Solution of HATU (0.3 M in DMF, 50 μl) was added and removed by centrifugation after 20 minutes incubation and solution of an amine (1 M in DMF, 40 μl) was added. After 1 hour incubation of closed multititerplates at shaker, the solution was removed by centrifugation, plates were washed by DMF (2 times) and preincubation with HATU and incubation with amine solution was repeated once more overnight. Solution was removed by centrifugation and multititerplates were washed with DMF five times and with tert.butylmethylether twice. Trifluoroacetic acid was added to the plates by multichannel pipettor (75 μl to each well) and closed plates were shaken for two hours. Multititerplates were then opened, placed into SpeedVac (Savant), TFA was evaporated in vacuo. Plates were placed onto the table of Multiprobe 104 and solid support was extracted by repeated (four times) addition and removal of 165 μl of DMF into individual wells of multititerplate. Extracts were transferred to deep well polypropylene microtiter plates and evaporated in SpeedVac. All wells were analyzed by LCMS. Purities of prepared compounds were ranked into four categories.

The results are presented in Table 2.

TABLE 2

Results of Synthesis of 380 Tetrahydroisoquinolone Compounds

| PRODUCT | NUMBER OF CASES | % |
|---|---|---|
| Single peak (>95%) | 201 | 52.90 |
| Major peak (85–95%) | 129 | 33.90 |

TABLE 2-continued

Results of Synthesis of 380 Tetrahydroisoquinolone Compounds

| PRODUCT | NUMBER OF CASES | % |
| --- | --- | --- |
| Product present (50–85%) | 14 | 3.70 |
| Minor peak (<50%) | 21 | 5.60 |
| Not present | 15 | 3.90 |

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A method for separating a liquid phase from a solid phase, comprising:
   (a) positioning an array of reaction vessels, said vessels containing a slurry of solid phase supports in a liquid, on the perimeter of a centrifuge rotor; and
   (b) spinning the rotor of the centrifuge at a speed so that the solid phase supports sediment in a pocket of the vessels from which material cannot be removed by centrifugal force and the liquid in excess of the volume of the pocket is expelled from the top of the vessels while spinning.

2. The method of claim 1, in which the array of reaction vessels is a microtiter plate and the vessels are spun at a tilted position at an angle of tilt which is not greater than 22 degrees tilting towards the center of rotation.

3. The method of claim 1, in which the array of reaction vessels is a microtiter plate with vessels having walls perpendicular to their bases, in which each vessel contains an individual solid phase support or an amount of solid phase supports that cannot form more than a monolayer on the side of the wall of the vessel and the vessels are spun at an angle of tilt which is zero degrees or the same value as the slope of the walls of the vessels.

4. The method of claim 1, in which the reaction vessels are one or more arrays of microtiter plates having standard size wells and the rotor and the spinning occurs with the plate at a tilt angle 1 to 45 degrees.

5. The method of claim 1, in which the reaction vessels are one or more arrays of microtiter plates having micro size wells and the rotor and the spinning occurs with the plate at a tilt angle 0 to 25 degrees.

6. A method for separating a liquid phase from a solid phase, comprising:
   (a) positioning an array of reaction vessels, said vessels containing a slurry of solid phase supports in a liquid, on the perimeter of a centrifuge rotor in a tilted position; and
   (b) spinning the rotor of the centrifuge at a speed at which the centrifugal force on the radius corresponding to the vessels which are closest to the axis of rotation is substantially greater than the force of gravity, so that the solid phase supports sediment in a pocket of the vessels from which material cannot be removed by centrifugal force and the liquid in excess of the volume of the pocket is expelled from the top of the vessels while spinning.

7. The method according to claim 6, in which the rotors of the centrifuge is spun at a speed at which the centrifugal force on the radius corresponding to the reaction vessels closest to the axis of rotation is at least 20× G.

8. The method according to claim 6, in which the rotor of the centrifuge is spun at a speed at which the centrifugal force on the radius corresponding to the reaction vessels closest to the axis of rotation is at least 5 to 300× G.

9. The method of claim 1 or 6, in which the method of separating is employed during a high-throughput solid phase organic synthesis of a combinatorial library of compounds.

10. The method according to claim 1 or claim 6 wherein the method of separating is employed during solid-phase synthesis of organic compounds.

11. The method according to claim 10, wherein said organic compounds are peptides.

12. The method according to claim 10, further comprising repeating steps (a) and (b).

13. The method according to claim 12 further comprising washing said solid phase supports prior to said repeating.

14. The method according to claim 1 or claim 6 wherein said reaction vessels comprise at least one microtiter plate.

15. The method according to claim 1 or claim 6 wherein said solid phase supports comprise beads.

16. The method according to claim 15, where in said beads are microbeads.

17. A method of solid-phase synthesis of compounds, said method comprising:
   (a) providing a reaction vessel containing a first building block coupled to a solid support in a slurry of solid supports in a liquid;
   (b) positioning said vessel on the perimeter of a centrifuge rotor;
   (c) spinning said rotor at a speed sufficient to expel said liquid from the top of said vessel while spinning and deposit said slurry of solid supports in a pocket of the vessel from which material cannot be removed by centrifugal force, wherein the liquid expelled is that in excess of the volume of the pocket; and
   (d) adding a second building block to said reaction vessel.

18. The method according to claim 17 wherein said positioning is in a tilted position.

19. The method according to claim 17 or claim 18 further comprising:
   (e) spinning said rotor at a speed sufficient to expel said liquid from the top of said vessel while spinning and deposit said slurry of solid supports in a pocket of the vessel from which material cannot be removed by centrifugal force, wherein the liquid expelled is that in excess of the volume of the pocket.

20. The method according to claim 17 or claim 18 further comprising washing said solid supports prior to step (d).

21. The method according to claim 17 or claim 18 wherein said reaction vessel is at least one microtiter plate.

22. The method according to claim 17 or claim 18 wherein said solid supports comprise beads.

23. The method according to claim 22, wherein said beads are microbeads.

24. The method according to claim 17 or claim 18 wherein said first or second building block is an organic acid.

25. The method according to claim 24, wherein said organic acid is an amino acid.

26. The method according to claim 17 or claim 18 wherein said second building block is added at a molar excess relative to said first building block coupled to said solid support.

27. The method according to claim 17 or claim 18 wherein said solid phase synthesis is solid phase organic synthesis.

* * * * *